US008815775B2

(12) United States Patent
Cristau et al.

(10) Patent No.: US 8,815,775 B2
(45) Date of Patent: Aug. 26, 2014

(54) BIS(DIFLUOROMETHYL)PYRAZOLES AS FUNGICIDES

(75) Inventors: Pierre Cristau, Lyons (FR); Sebastian Hoffmann, Neuss (DE); Joachim Kluth, Langenfeld (DE); Thomas Seitz, Langenfeld (DE); Tomoki Tsuchiya, Düsseldorf (DE); Pierre Wasnaire, Düsseldorf (DE); Jürgen Benting, Leichlingen (DE); Ulrike Wachendorff-Neumann, Neuwied (DE)

(73) Assignee: Bayer CropScience AG, Monheim (DE)

( * ) Notice: Subject to any disclaimer, the term of this patent is extended or adjusted under 35 U.S.C. 154(b) by 245 days.

(21) Appl. No.: 13/108,496

(22) Filed: May 16, 2011

(65) Prior Publication Data

US 2011/0301197 A1    Dec. 8, 2011

Related U.S. Application Data

(60) Provisional application No. 61/345,796, filed on May 18, 2010.

(30) Foreign Application Priority Data

May 18, 2010 (EP) ..................................... 10163067

(51) Int. Cl.
  *C07D 417/14* (2006.01)
  *A01N 43/40* (2006.01)
  *A01N 43/56* (2006.01)

(52) U.S. Cl.
  USPC ........... 504/249; 546/184; 546/192; 546/209; 504/244; 504/248

(58) Field of Classification Search
  USPC ........... 546/184, 207, 209; 504/244, 248, 249
  See application file for complete search history.

(56) References Cited

U.S. PATENT DOCUMENTS

| 4,245,432 | A | 1/1981 | Dannelly |
| 4,272,417 | A | 6/1981 | Barke et al. |
| 4,808,430 | A | 2/1989 | Kouno |
| 5,876,739 | A | 3/1999 | Turnblad et al. |
| 5,925,645 | A | 7/1999 | Schmidt et al. |
| 2003/0176428 | A1 | 9/2003 | Schneidersmann et al. |
| 2010/0056569 | A1 | 3/2010 | Nan et al. |
| 2011/0105429 | A1 | 5/2011 | Cristau et al. |

FOREIGN PATENT DOCUMENTS

| WO | WO 96/33270 A1 | 10/1996 |
| WO | WO 02/28186 A2 | 4/2002 |
| WO | WO 02/080675 A1 | 10/2002 |
| WO | WO 2004/108692 A1 | 12/2004 |
| WO | WO 2006/133216 A2 | 12/2006 |
| WO | WO 2007/014290 A2 | 2/2007 |
| WO | WO 2007/024782 A2 | 3/2007 |
| WO | WO 2007/027777 A2 | 3/2007 |
| WO | WO 2008/013622 A2 | 1/2008 |
| WO | WO 2008/013925 A2 | 1/2008 |
| WO | WO 2008/091580 A2 | 7/2008 |
| WO | WO 2008/091594 A2 | 7/2008 |
| WO | WO 2009/037357 A1 | 3/2009 |
| WO | WO 2009/055514 A2 | 4/2009 |
| WO | WO 2009/094407 A2 | 7/2009 |
| WO | WO 2009/094445 A2 | 7/2009 |

OTHER PUBLICATIONS

Albrecht, B. K., et al., "Discovery and optimization of substituted piperidines as potent, selective, CNS-penetrant α4β2 nicotinic acetylcholine receptor potentiators," *Bioorganic & Medicinal Chemistry Letters* 18:5209-5212, Elsevier Ltd., England (2008).

Chambers, R.J. and Marfat, A., "Regiospecific Carboalkoxylation of 2,5-Dibromopyridine," *Synthetic Communications* 27(3):515-520, Pfizer Central Research, Marcel Dekker, United States (1997).

Chen, Y.L., et al., "Synthesis and β-Lactamase Inhibitory Activity of Thiazolyl Penam Sulfones," *The Journal of Antibiotics* 41(1):134-138, Japan Antibiotics Research Assn., Japan (1988).

Dvorko, G.F., et al., "Kinetics and Mechanism of Unimolecular Heterolysis of Cage-Like Compounds: XIX. Effect of the Nucleofuge Nature on the Activation Parameters of Heterolysis of 1-Halo-1-methylcyclohexanes in Cyclohexane, Heterolysis Rate Ratio in Aprotic and Protic Solvents," *Russian Journal of Organic Chemistry* 43(1):50-55, Pleiades Publishing, Ltd., Russia (2007).

El-Ghayoury, A. and Ziessel, R., "Facile Synthesis of Polypyridine Esters: A Route to Functionalized Aldehydes," *J. Org. Chem.* 65:7757-7763, American Chemical Society, United States (2000).

Jensen, O.E. and Senning, A., "Studies on Amino Acids and Peptides XII Synthesis of Thiated Analogues of Boc-S-Ala-Aib-S-Ala-OMe and Ac-S-Ala-Aib-S-Ala-Ome," *Tetrahedron* 42(23):6555-6564, Pergamon Journals Ltd., England (1986).

(Continued)

*Primary Examiner* — Golam M M Shameem
(74) *Attorney, Agent, or Firm* — Sterne, Kessler, Goldstein & Fox P.L.L.C.

(57) ABSTRACT

Bis(difluoromethyl)pyrazole derivatives of the formula (I)

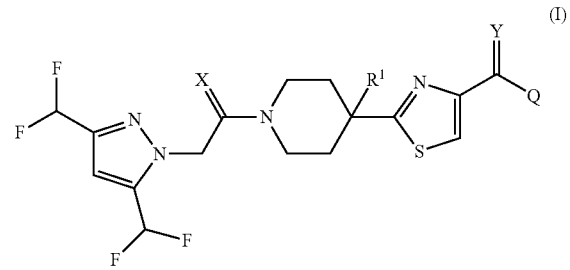

in which the symbols $R^1$, X, Y and Q are each as defined in the description, and agrochemically active salts thereof, and use thereof for controlling phytopathogenic harmful fungi, and also processes for preparing compounds of the formula (I).

13 Claims, No Drawings

(56) References Cited

OTHER PUBLICATIONS

Montalbetti, C.A.G.N. and Falque, V., "Amide bond formation and peptide coupling," *Tetrahedron 61*:10827-10852, Elsevier Ltd., England (2005).

Mylari, B.L., et al., "Novel, Potent Aldose Reductase Inhibitors: 3,4-Dihydro-4-oxo-3-[[5-(trifluoromethyl)-2-benzothiazolyl]methyl]-1-phthalazineacetic Acid (Zopolrestat) and Congeners," *J. Med Chem. 34*:108-122, American Chemical Society, United States (1991).

Ohmiya, H., et al., "Cobalt-Catalyzed Cross-Coupling Reactions of Alkyl Halides with Allylic and Benzylic Grignard Reagents and Their Application to Tandem Radical Cyclization/Cross-Coupling Reactions," *Chem. Eur. J. 10*:5640-5648, Wiley-VCH Verlag GmbH & Co. KGaA, Weinheim, Germany (2004).

Rodik, R., et al., "Calix[4]arenesulfonylamidines. Synthesis, structure and influence on $Mg^{2+}$, ATP-dependent calcium pumps," *Tetrahedron Letters 46*:7459-7462, Elsevier Ltd., England (2005).

Shao, J. and Panek, J.S., "Total Synthesis of Cystothiazoles A and B," *Org. Lett.* 6(18):3083-3085, American Chemical Society, United States (2004).

Wardell, J.L., "Preparation of thiols," in *The chemistry of the thiol group*, Part 1, p. 163-269, Patai, S., ed., John Wiley & Sons, Ltd., England (1974).

International Search Report for Inernational Application No. PCT/EP2011/057912, European Patent Office, The Hague, Netherlands, mailed on Jul. 6, 2011.

BIS(DIFLUOROMETHYL)PYRAZOLES AS FUNGICIDES

The present invention relates to novel bis(difluoromethyl) pyrazole derivatives, to processes for preparation thereof, to the use thereof for controlling unwanted microorganisms, especially phytopathogenic fungi, in crop protection, in the domestic and hygiene sectors and in the protection of materials, and also to crop protection compositions comprising these bis(difluoromethyl)pyrazole derivatives.

It is already known that particular substituted pyrazole derivatives can be used as fungicidal crop protection compositions (see WO 2007/014290, WO 2008/013925, WO 2008/013622, WO 2008/091594, WO 2008/091580, WO 2009/055514, WO 2009/094407, WO 2009/094445). However, specifically at relatively low application rates, the fungicidal efficacy of these compounds is not always sufficient.

Since the ecological and economic demands made on modern crop protection compositions are increasing constantly, for example with respect to activity spectrum, toxicity, selectivity, application rate, formation of residues and favourable manufacture, and there can also be problems, for example, with resistances, it is a constant objective to develop novel crop protection compositions, especially fungicides, which have advantages over the known compositions at least in some areas.

It has now been found that, surprisingly, the present bis (difluoromethyl)pyrazole derivatives achieve at least some aspects of the objects mentioned and are suitable for use as crop protection compositions, especially as fungicides.

The invention provides compounds of the formula (I)

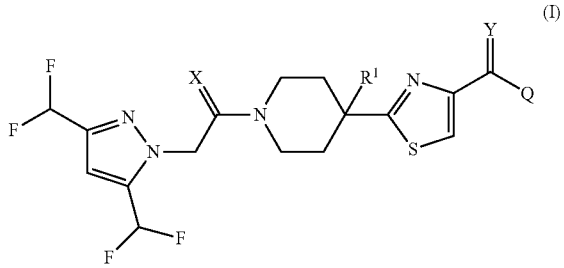

(I)

in which the symbols are each defined as follows:
X is oxygen or sulphur,
$R^1$ is hydrogen or halogen,
Y is oxygen or sulphur,
Q is $-NR^2R^3$,
$R^2$ is hydrogen, $C_1$-$C_3$-alkyl, $C_2$-$C_3$-alkenyl, $C_2$-$C_3$-alkynyl, $C_4$-$C_{10}$-cycloalkylalkyl, $C_4$-$C_{10}$ alkylcycloalkyl, $C_5$-$C_{10}$-alkylcycloalkylalkyl, $C_1$-$C_3$-haloalkyl, $C_2$-$C_3$-haloalkenyl, cyano, hydroxyl, $C_1$-$C_3$-alkoxy, $C_2$-$C_3$-alkoxyalkyl, $C_1$-$C_3$-hydroxyalkyl, $C_2$-$C_3$-alkylcarbonyl, $C_2$-$C_3$-alkoxycarbonyl, $C_2$-$C_3$-alkylaminocarbonyl or $C_3$-$O_5$-dialkylaminocarbonyl,
$R^3$ is an 8- to 11-membered, unsubstituted or substituted, saturated or partly saturated bicyclic ring system or is a 10- to 15-membered, unsubstituted or substituted, saturated or partly saturated tricyclic ring system; each ring system may optionally contain one to three heteroatoms (up to one oxygen atom, up to one sulphur atom and up to three nitrogen atoms) and optionally one to three ring members which may be selected from the group of C(=O), C(=S), S(=O) and S(=O)$_2$ or
$R^2$ and $R^3$ form, together with the nitrogen atom to which they are bonded, a 5- or 6-membered, unsubstituted or substituted, saturated or partly saturated heterocyclyl radical
or
$R^3$ is $-CR^4R^5R^6$,
$R^4$ is hydrogen, $C_1$-$C_6$-alkyl, $C_2$-$C_6$-alkenyl, $C_2$-$C_6$-alkynyl, $C_3$-$C_6$-cycloalkyl, $C_4$-$C_{10}$-cycloalkylalkyl, $C_4$-$C_{10}$-alkylcycloalkyl, $C_5$-$C_{10}$-alkylcycloalkylalkyl, $C_1$-$C_6$-haloalkyl, $C_2$-$C_6$-haloalkenyl, $C_2$-$C_6$-haloalkynyl, $C_3$-$C_6$-halocycloalkyl, cyano, nitro, $C_2$-$C_4$-alkoxyalkyl, $C_1$-$C_4$-hydroxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl or $C_3$-$C_6$-trialkylsilyl,
$R^5$ is unsubstituted or substituted phenyl, benzyl, naphthalenyl, $C_3$-$C_6$-cycloalkyl, $C_3$-$C_6$-cycloalkenyl or a 5- or 6-membered heteroaryl radical,
$R^6$ is hydrogen, $C_1$-$C_4$-alkyl, $C_2$-$C_4$-alkenyl, $C_2$-$C_4$-alkynyl, $C_3$-$C_4$-cycloalkyl, $C_4$-$C_{10}$-cycloalkylalkyl, $C_4$-$C_{10}$-alkylcycloalkyl, $C_5$-$C_{10}$-alkylcycloalkylalkyl, $C_1$-$C_4$-haloalkyl, $C_2$-$C_4$-haloalkenyl, $C_2$-$C_4$-haloalkynyl, $C_3$-$C_4$-halocycloalkyl or $C_2$-$C_4$-alkoxyalkyl,
or
$R^2$ and $R^4$ form, together with the atoms to which they are bonded, a 5- to 7-membered, unsubstituted or substituted ring system consisting of two to seven carbon atoms and optionally one to three heteroatoms (up to one oxygen atom, up to one sulphur atom and up to two nitrogen atoms),
or
$R^2$ and $R^5$ form, together with the atoms to which they are bonded, a 5- to 7-membered, unsubstituted or substituted ring system consisting of two to seven carbon atoms and optionally one to three heteroatoms (up to one oxygen atom, up to one sulphur atom and up to two nitrogen atoms),
or
$R^4$ and $R^6$ form, together with the carbon to which they are bonded, a 5- to 7-membered, unsubstituted or substituted ring system consisting of two to seven carbon atoms and optionally one to three heteroatoms (up to one oxygen atom, up to one sulphur atom and up to one nitrogen atom),
or
$R^4$ and $R^5$ form, together with the carbon to which they are bonded, a 5- to 7-membered, unsubstituted or substituted ring system consisting of two to seven carbon atoms and optionally one to three heteroatoms (up to one oxygen atom, up to one sulphur atom and up to one nitrogen atom),
and agrochemically active salts thereof.

The invention further provides for the use of the compounds of the formula (I) as fungicides.

Inventive bis(difluoromethyl)pyrazole derivatives of the formula (I) and the agrochemically active salts thereof are very suitable for controlling phytopathogenic harmful fungi. The aforementioned inventive compounds exhibit, in particular, potent fungicidal activity and can be used in crop protection, in the domestic and hygiene sector and in the protection of materials.

The compounds of the formula (I) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and the Z isomers are claimed, as are the threo and erythro isomers, and also the optical isomers, any mixtures of these isomers, and also the possible tautomeric forms.

The bis(difluoromethyl)pyrazole derivatives usable in accordance with the invention are defined in general terms by the formula (I). Preferred radical definitions for the formulae specified above and below are given below. These definitions apply equally to the end products of the formula (I) and to all intermediates (see also below under "Illustrations of the processes and intermediates").

X is preferably oxygen, $R^1$ is preferably hydrogen or fluorine,

Y is preferably oxygen,

Q is preferably

Q1=

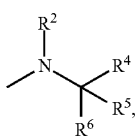

Q2=

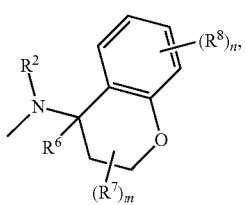

Q3=

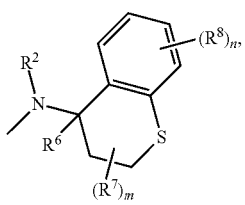

Q4=

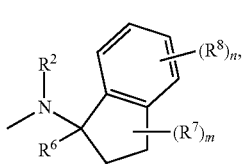

Q5=

Q6=

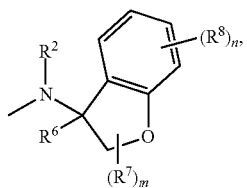

Q7=

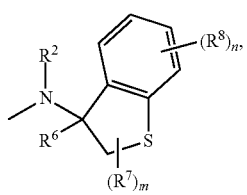

Q8=

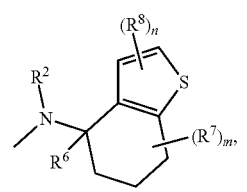

Q9=

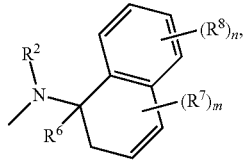

Q10=

Q11=

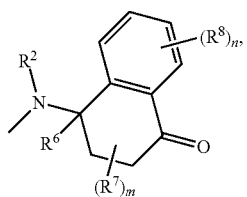

Q12= 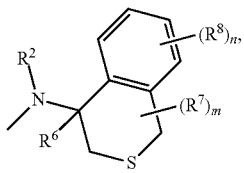

Q13= 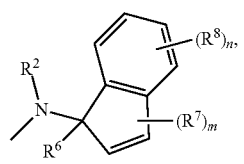

Q14= 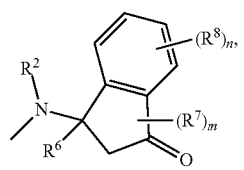

Q15= 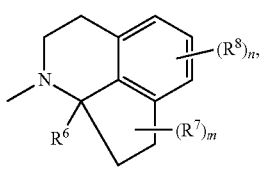

Q16= 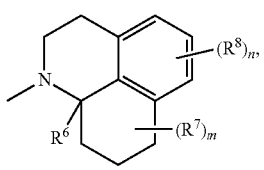

Q17= 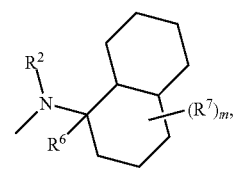

Q18= 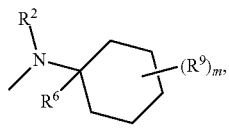

Q is more preferably Q1, Q2, Q5, Q9, Q11, Q14, Q15 or Q16,
Q is even more preferably Q2, Q5 or Q9,
Q is especially preferably Q2,
m is preferably 0, 1 or 2,
m is more preferably 0 or 1,
m is even more preferably 0,
n is preferably 0, 1 or 2,
n is more preferably 0 or 1,
n is even more preferably 0,
$R^2$ is preferably hydrogen or $C_1$-$C_3$-alkyl,
$R^2$ is more preferably hydrogen, methyl, ethyl or isopropyl,
$R^2$ is even more preferably hydrogen or methyl,
$R^4$ is preferably hydrogen, $C_1$-$C_4$-alkyl, $C_3$-$C_6$-cycloalkyl, $C_2$-$C_4$-alkoxyalkyl, $C_1$-$C_6$-haloalkyl,
$R^4$ is more preferably hydrogen or $C_1$-$C_4$-alkyl,
$R^4$ is even more preferably hydrogen, methyl or ethyl,
$R^5$ is preferably unsubstituted or substituted phenyl, benzyl or $C_3$-$C_6$-cycloalkyl,
$R^5$ is more preferably phenyl which may contain up to three substituents, where the substituents are each independently selected from the following list: halogen, cyano, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl. $C_3$-$C_8$-cycloalkyl, $C_3$-$C_8$-halocycloalkyl, $C_2$-$C_6$-alkoxyalkyl, $C_2$-$C_6$-alkylcarbonyl, $C_2$-$C_6$-haloalkynyl, $C_3$-$C_8$-haloalkylcarbonyl, $C_2$-$C_6$-alkoxycarbonyl, $C_1$-$C_6$-alkoxy, $C_1$-$C_6$-haloalkoxy, $C_3$-$C_8$-cycloalkoxy, $C_3$-$C_8$-halocycloalkoxy, $C_2$-$C_6$-alkenyloxy, $C_2$-$C_6$-alkynyloxy, $C_2$-$C_6$-alkynyloxy, $C_2$-$C_6$-alkoxyalkoxy, $C_1$-$C_6$-alkylthio, $C_1$-$C_6$-haloalkylthio, $C_1$-$C_6$-alkylsulphinyl, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl or tri($C_1$-$C_4$-alkyl)silyl,
$R^5$ is even more preferably phenyl which may contain up to three substituents, where the substituents are each independently selected from the following list: chlorine, fluorine, bromine, iodine, cyano, nitro, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)CH_3$, —$C(CH_3)_3$, —$CH=CH_2$, —$CH=CHCH_3$, —$CH_2CH=CH_2$, —$CH=CHCH_2CH_3$, —$CH_2CH=CHCH_3$, —$CH_2CH_2CH=CH_2$, —$C≡CH$, —$C≡CCH_3$, —$CH_2C≡CH$, —$C≡CCH_2CH_3$, —$CH_2C≡CCH_3$, —$CH_2CH_2C≡CH$, —$CF_3$, —$CFH_2$, —$CF_2H$, —$CF_2CF_3$, —$CCl_3$, cyclopropyl, cyclobutyl, cyclopentyl, cyclohexyl, —$CH_2OCH_3$, —$CH_2OCH_2CH_3$, —$CH_2CH_2OCH_3$, —$CH_2OCH_2CH_2CH_3$, —$CH_2CH_2OCH_2CH_3$, —$CH_2CH_2CH_2OCH_3$, —$C(=O)CH_3$, —$C(=O)CH_2CH_3$, $C(=O)CH_2CH_2CH_3$, $C(=O)CH(CH_3)_2$, —$C(=O)CF_3$, —$C(=O)OCH_3$, —$C(=O)OCH_2CH_3$, —$C(=O)OCH_2CH_2CH_3$, —$C(=O)OCH(CH_3)_2$, —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH(CH_3)CH_2CH_3$, —$OC(CH_3)_3$, —$OCF_3$, —$OCF_2H$, —$OCH_2CF_3$, —$OCF_2CF_3$, O-cyclohexyl, O-cyclopentyl, O-cyclopropyl, —$SCH_3$, —$SCH_2CH_3$, —$SCH_2CH_2CH_3$, —$SCH(CH_3)_2$, —$SCH_2CH_2CH_2CH_3$, —$SCH_2CH(CH_3)_2$, —$SCH(CH_3)CH_2CH_3$, —$SC(CH_3)_3$, —$SCF_3$, —$SCF_2H$, —$SCH_2CF_3$, —$SCF_2CF_3$, —$S(=O)Me$, —S(O)CF$_3$, —S(=O)$_2$Me, —S(O)$_2$CF$_3$, —OCH$_2$CH=CH$_2$, —OCH$_2$C≡CH, —OCH$_2$OCH$_3$, —OCH$_2$OCH$_2$CH$_3$, —OCH$_2$CH$_2$OCH$_3$, —OCH$_2$OCH(CH$_3$)$_2$ or trimethylsilyl, R$^6$ is preferably hydrogen or C$_1$-C$_4$-alkyl, C$_3$-C$_4$-cycloalkyl, C$_2$-C$_4$-alkoxyalkyl, C$_1$-C$_4$-haloalkyl, R$^6$ is more preferably hydrogen or C$_1$-C$_4$-alkyl, R$^6$ is even more preferably hydrogen, methyl or ethyl, R$^7$ is preferably in each case independently hydrogen, C$_1$-C$_4$-alkyl, halogen, cyano, hydroxyl, amino, nitro, C$_2$-C$_4$-alkenyl, C$_3$-C$_4$-alkynyl, C$_1$-C$_4$-haloalkyl, C$_2$-C$_4$-haloalkenyl, C$_2$-C$_4$-haloalkyl, C$_3$-C$_6$-cycloalkyl, C$_3$-C$_6$-halocycloalkyl, C$_2$-C$_4$-alkoxyalkyl, C$_1$-C$_4$-alkylamino C$_2$-C$_6$-dialkylamino, C$_3$-C$_6$-cycloalkylamino, C$_2$-C$_4$-alkylcarbonyl, C$_2$-C$_4$-alkoxycarbonyl, C$_2$-C$_4$-alkylaminocarbonyl, C$_2$-C$_4$-alkylaminocarbonyloxy, C$_3$-C$_6$-dialkylaminocarbonyl, C$_1$-C$_4$-hydroxyalkyl, C$_1$-C$_4$-alkoxy, C$_1$-C$_4$-haloalkoxy, C$_2$-C$_4$-alkylcarbonyloxy, C$_2$-C$_4$-alkylcarbonylthio, C$_1$-C$_4$-alkylthio, C$_1$-C$_4$-haloalkylthio, C$_1$-C$_4$-alkylsulphinyl, C$_1$-C$_4$-haloalkylsulphinyl, C$_1$-C$_4$-alkylsulphonyl, C$_1$-C$_4$-haloalkylsulphonyl or tri(C$_1$-C$_2$-alkyl)silyl, R$^7$ is more preferably in each case independently hydrogen, C$_1$-C$_4$-alkyl, halogen, cyano, hydroxyl, amino, nitro, C$_2$-C$_4$-alkenyl, C$_3$-C$_4$-alkynyl, C$_1$-C$_4$-haloalkyl, C$_2$-C$_4$-haloalkenyl, C$_2$-C$_4$-haloaknyl, C$_3$-C$_6$-cycloalkyl, C$_3$-C$_6$-halocycloalkyl, C$_1$-C$_4$-alkoxy or C$_2$-C$_4$-alkylcarbonyloxy, R$^7$ is even more preferably in each case independently hydrogen, methyl, ethyl, —CF$_3$, —CFH$_2$, —CF$_2$H, —CF$_2$CF$_3$, —CCl$_3$, —OCH$_3$, —OCH$_2$CH$_3$, —OCF$_3$, —OCF$_2$H, —OCH$_2$CF$_3$, —OCF$_2$CF$_3$, —OC(=O)CH$_3$, —OC(=O)CH$_2$CH$_3$, —OC(=O)CH$_2$CH$_2$CH$_3$, —OC(=O)CH(CH$_3$)$_2$ or hydroxyl, R$^8$ is preferably in each case independently C$_1$-C$_6$-alkyl, halogen, cyano, hydroxyl, amino, nitro, C$_2$-C$_6$-alkenyl, C$_3$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_3$-C$_6$-halocycloalkyl, C$_2$-C$_4$-alkoxyalkyl, C$_1$-C$_4$-alkylamino, C$_2$-C$_8$-dialkylamino, C$_3$-C$_6$-cycloalkylamino, C$_2$-C$_4$-alkylcarbonyl, C$_2$-C$_6$-alkoxycarbonyl, C$_2$-C$_6$-alkylaminocarbonyl, C$_3$-C$_8$-dialkylaminocarbonyl, C$_1$-C$_4$-hydroxyalkyl, C$_1$-C$_4$-alkoxy, C$_1$-C$_4$-haloalkoxy, C$_2$-C$_6$-alkylcarbonyloxy, C$_2$-C$_6$-alkylcarbonylthio, C$_1$-C$_4$-alkylthio, C$_1$-C$_4$-haloalkylthio, C$_1$-C$_4$-alkylsulphinyl, C$_1$-C$_4$-haloalkylsulphinyl, C$_1$-C$_4$-alkylsulphonyl, C$_1$-C$_4$-haloalkylsulphonyl or tri(C$_1$-C$_2$-alkyl)silyl, R$^8$ is more preferably in each case independently C$_1$-C$_3$-alkyl, cyclopropyl, halogen, hydroxyl, C$_1$-C$_3$-haloalkyl, halocyclopropyl, C$_1$-C$_2$-alkoxy, C$_1$-C$_2$-haloalkoxy or C$_2$-C$_3$-alkylcarbonyloxy, R$^8$ is even more preferably in each case independently fluorine, chlorine, bromine, iodine, hydroxyl, methyl or —OCH$_3$, R$^9$ is preferably independently C$_1$-C$_6$-alkyl, halogen, cyano, hydroxyl, amino, nitro, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_4$-C$_{10}$-cycloalkylalkyl, C$_4$-C$_{10}$-alkylcycloalkyl, C$_5$-C$_{10}$-alkylcycloalkylalkyl, C$_3$-C$_6$-halocycloalkyl, C$_2$-C$_4$-alkoxyalkyl, C$_1$-C$_4$-alkylamino, C$_2$-C$_8$-dialkylamino, C$_3$-C$_6$-cycloalkylamino, C$_2$-C$_4$-alkylcarbonyl, C$_2$-C$_6$-alkoxycarbonyl, C$_2$-C$_6$-alkylaminocarbonyl, C$_3$-C$_8$-dialkylaminocarbonyl, C$_1$-C$_4$-hydroxyalkyl, C$_1$-C$_4$-alkoxy, C$_1$-C$_4$-haloalkoxy, C$_2$-C$_6$-alkylcarbonyloxy, C$_2$-C$_6$-alkylcarbonylthio, C$_1$-C$_4$-alkylthio, C$_1$-C$_4$-haloalkylthio, C$_1$-C$_4$-alkylsulphinyl, C$_1$-C$_4$-haloalkylsulphinyl, C$_1$-C$_4$-alkylsulphonyl, C$_1$-C$_4$-haloalkylsulphonyl, tri(C$_1$-C$_2$-alkyl)silyl or R$^9$ is preferably independently phenyl or benzyl which may contain up to three substituents, where the substituents are each independently selected from the following list: C$_1$-C$_3$-alkyl, halogen, cyano, nitro, C$_2$-C$_3$-alkenyl, C$_2$-C$_3$-alkynyl, cyclopropyl, C$_1$-C$_3$-haloalkyl, C$_2$-C$_3$-haloalkenyl, C$_2$-C$_3$-haloalkynyl, halocyclopropyl, C$_1$-C$_2$-alkoxy or C$_1$-C$_2$-haloalkoxy R$^9$ is more preferably independently C$_1$-C$_6$-alkyl, halogen, cyano, hydroxyl, C$_1$-C$_6$-haloalkyl, C$_3$-C$_6$-cycloalkyl, C$_1$-C$_4$-alkoxy, C$_1$-C$_4$-haloalkoxy, C$_1$-C$_4$-alkylthio, C$_1$-C$_4$-haloalkylthio or tri(C$_1$-C$_2$-alkyl)silyl or R$^9$ is more preferably independently phenyl which may contain up to three substituents, where the substituents are each independently selected from the following list: C$_1$-C$_3$-alkyl, halogen, cyano, nitro, C$_2$-C$_3$-alkenyl, C$_2$-C$_3$-alkynyl, C$_1$-C$_3$-haloalkyl, C$_1$-C$_2$-alkoxy or C$_1$-C$_2$-haloalkoxy, R$^9$ is even more preferably independently chlorine, fluorine, bromine, iodine, cyano, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)CH$_3$, —C(CH$_3$)$_3$, —CF$_3$, —CFH$_2$, —CF$_2$H, —CF$_2$CF$_3$, —CCl$_3$, cyclopropyl, cyclobutyl, cyclopentyl, cyclohexyl, —OCH$_3$, —OCH$_2$CH$_3$, —OCH$_2$CH$_2$CH$_3$, —OCH(CH$_3$)$_2$, —OCH$_2$CH$_2$CH$_2$CH$_3$, —OCH$_2$CH(CH$_3$)$_2$, —OCH(CH$_3$)CH$_2$CH$_3$, OC(CH$_3$)$_3$, —OCF$_3$, —OCF$_2$H, —OCH$_2$CF$_3$, —OCF$_2$CF$_3$, —SCH$_3$, —SCH$_2$CH$_3$, —SCH$_2$CH$_2$CH$_3$, —SCH(CH$_3$)$_2$, —SCH$_2$CH$_2$CH$_3$, —SCH$_2$CH(CH$_3$)$_2$, —SCH(CH$_3$)CH$_2$CH$_3$, —SC(CH$_3$)$_3$, —SCF$_3$, —SCF$_2$H, —SCH$_2$CF$_3$, —SCF$_2$CF$_3$ or trimethylsilyl, or R$^9$ is even more preferably independently phenyl which may contain up to three substituents, where the substituents are each independently selected from the following list: —CH$_3$, —CH$_2$CH$_3$, —CH$_2$CH$_2$CH$_3$, —CH(CH$_3$)$_2$, chlorine, fluorine, bromine, iodine, cyano, —CH=CH$_2$, —CH=CHCH$_3$, —CH$_2$CH=CH$_2$, —C≡CH, —C≡CCH$_3$, —CH$_2$C≡CH, —CF$_3$, —CFH$_2$, —CF$_2$H, —CF$_2$CF$_3$, —CCl$_3$, —OCH$_3$, —OCH$_2$CH$_3$, —OCF$_3$, —OCF$_2$H, —OCH$_2$CF$_3$ or —OCF$_2$CF$_3$ and agrochemically active salts thereof.

The radical definitions and explanations given above in general terms or stated within areas of preference can, however, also be combined with one another as desired, i.e. including between the particular areas and preferred areas of preference. They apply both to the end products and correspondingly to precursors and intermediates. In addition, individual definitions may not apply.

Preference is given to compounds of the formula (I) in which each of the radicals have the abovementioned preferred definitions.

Particular preference is given to compounds of the formula (I) in which each of the radicals have the abovementioned more preferred definitions.

Very particular preference is given to compounds of the formula (I) in which each of the radicals have the abovementioned even more preferred definitions.

Special preference is given to compounds of the formula (I) in which each of the radicals have the abovementioned especially preferred definitions.

Preference is further given to compounds of the formula (I) in which X is oxygen, and to agrochemically active salts thereof.

Preference is further given to compounds of the formula (I) in which Y is oxygen, and to agrochemically active salts thereof.

Preference is further given to compounds of the formula (I) in which $R^1$ is hydrogen, and to agrochemically active salts thereof.

Preference is further given to compounds of the formula (I) in which $R^1$ is fluorine, and to agrochemically active salts thereof.

Preference is further given to compounds of the formula (I) in which Q is
Q2a=

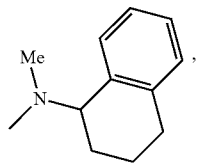

and to agrochemically active salts thereof.

Preference is further given to compounds of the formula (I) in which Q is
Q2b=

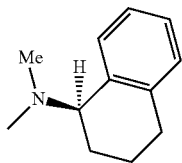

and to agrochemically active salts thereof.

Preference is further given to compounds of the formula (I) in which Q is
Q2c=

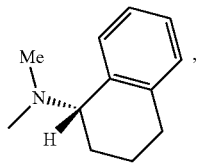

and to agrochemically active salts thereof.

According to the nature of the substituents defined above, the compounds of the formula (I) have acidic or basic properties and can form salts, and if appropriate also inner salts or adducts with inorganic or organic acids or with bases or with metal ions. If the compounds of the formula (I) bear amino, alkylamino or other groups which induce basic properties, these compounds can be reacted with acids to give salts, or they are obtained directly as salts by the synthesis. If the compounds of the formula (I) bear hydroxyl, carboxyl or other groups which induce acidic properties, these compounds can be reacted with bases to give salts. Suitable bases are, for example, hydroxides, carbonates, hydrogencarbonates of the alkali metals and alkaline earth metals, especially those of sodium, potassium, magnesium and calcium, and also ammonia, primary, secondary and tertiary amines having $C_1$-$C_4$-alkyl groups, mono-, di- and trialkanolamines of $C_1$-$C_4$-alkanols, choline and also chlorocholine.

The salts obtainable in this way likewise have fungicidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as $NaHSO_4$ and $KHSO_4$. As organic acids come, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$ fatty acids, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Useful metal ions are especially the ions of the elements of the second main group, especially calcium and magnesium, of the third and fourth main group, especially aluminium, tin and lead, and also of the first to eighth transition groups, especially chromium, manganese, iron, cobalt, nickel, copper, zinc and others. Particular preference is given to the metal ions of the elements of the fourth period. The metals may be present in the different valences that they can assume.

Optionally substituted groups may be mono- or polysubstituted, where the substituents in the case of polysubstitutions may be identical or different.

In the definitions of the symbols given in the above formulae, collective terms were used which are generally representative of the following substituents:

halogen: fluorine, chlorine, bromine and iodine;

alkyl: saturated, straight-chain or branched hydrocarbon radicals having 1 to 8 carbon atoms, for example (but not limited thereto) $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methyl-butyl, 2,2-dimethylpropyl, 1-ethylpropyl, hexyl, 1,1-dimethylpropyl, 1,2-dimethylpropyl, 1-methyl-pentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkenyl: unsaturated, straight-chain or branched hydrocarbon radicals having 2 to 8 carbon atoms and a double bond in any position, for example (but not limited thereto) $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-prop enyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-1-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 8 carbon atoms and a triple bond in any position, for example (but not limited thereto) $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkoxy: saturated, straight-chain or branched alkoxy radicals having 1 to 8 carbon atoms, for example (but not limited thereto) $C_1$-$C_6$-alkoxy, such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethyl-propoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

alkylthio: saturated, straight-chain or branched alkylthio radicals having 1 to 8 carbon atoms, for example (but not limited thereto) $C_1$-$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethyl-propylthio, 1-ethyl-1-methylpropylthio and 1-ethyl-2-methylpropylthio;

alkoxycarbonyl: an alkoxy group having 1 to 6 carbon atoms (as mentioned above) which is attached to the skeleton via a carbonyl group (—CO—);

alkylsulphinyl: saturated, straight-chain or branched alkylsulphinyl radicals having 1 to 8 carbon atoms, for example (but not limited thereto) $C_1$-$C_6$-alkylsulphinyl, such as methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl;

alkylsulphonyl: saturated, straight-chain or branched alkylsulphonyl radicals having 1 to 8 carbon atoms, for example (but not limited thereto) $C_1$-$C_6$-alkylsulphonyl, such as methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl;

cycloalkyl: monocyclic saturated hydrocarbon groups having 3 to 10 carbon ring members, for example (but not limited thereto) cyclopropyl, cyclopentyl and cyclohexyl;

haloalkyl: straight-chain or branched alkyl groups having 1 to 8 carbon atoms (as mentioned above), where in these groups some or all of the hydrogen atoms may be replaced by halogen atoms as mentioned above, for example (but not limited thereto) $C_1$-$C_3$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

haloalkoxy: straight-chain or branched alkoxy groups having 1 to 8 carbon atoms (as mentioned above), where in these groups some or all of the hydrogen atoms may be replaced by halogen atoms as mentioned above, for example (but not limited thereto) $C_1$-$C_3$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy;

haloalkylthio: straight-chain or branched alkylthio groups having 1 to 8 carbon atoms (as mentioned above), where in these groups some or all of the hydrogen atoms may be replaced by halogen atoms as mentioned above, for example (but not limited thereto) $C_1$-$C_3$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-di-fluoroethylthio, 2,2-dichloro-2-fluoroethylthio, 2,2,2-trichloroethylthio, pentafluoroethylthio and 1,1,1-trifluoroprop-2-ylthio;

heteroaryl: a 5 or 6-membered fully unsaturated monocyclic ring system comprising one to four heteroatoms from the group consisting of oxygen, nitrogen and sulphur; if the ring contains a plurality of oxygen atoms, these are not directly adjacent;

5-membered heteroaryl: containing one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited to) 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

5-membered heteroaryl which contains one to four nitrogen atoms and is attached via nitrogen or benzofused 5-membered heteroaryl which contains one to three nitrogen atoms and is attached via nitrogen: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, for example (but not limited to) 1-pyrrolyl, 1-pyrazolyl, 1,2,4-triazol-1-yl, 1-imidazolyl, 1,2,3-triazol-1-yl and 1,3,4-triazol-1-yl;

6-membered heteroaryl containing one to four nitrogen atoms: 6-membered heteroaryl groups which, in addition to carbon atoms, may contain one to three or one to four nitrogen atoms as ring members, for example (but not limited to) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzofused 5-membered heteroaryl containing one to three nitrogen atoms or one nitrogen atom and one oxygen or sulphur atom: for example (but not limited to) indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl, benzofused 6-membered heteroaryl containing one to three nitrogen atoms: for example (but not limited to) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl;

heterocyclyl: a three- to fifteen-membered saturated or partially unsaturated heterocycle containing one to four heteroatoms from the group consisting of oxygen, nitrogen and sulphur: mono-, bi- or tricyclic heterocycles which contain, in addition to carbon ring members, one to three nitrogen atoms and/or one oxygen or sulphur atom or one or two oxygen and/or sulphur atoms; if the ring contains a plurality of oxygen atoms, these are not directly adjacent; such as, for example (but not limited thereto), oxiranyl, aziridinyl, 2-tetrahydrofuranyl, 3-tetrahydrofuranyl, 2-tetrahydrothienyl, 3-tetra-hydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

Not included are combinations which contravene the laws of nature and which the person skilled in the art would therefore rule out on the basis of his/her expert knowledge. Ring structures having three or more adjacent oxygen atoms, for example, are excluded.

Illustration of the Processes and Intermediates

The bis(difluoromethyl)pyrazole derivatives of the formula (I) can be prepared in different ways. First of all, the possible processes are shown schematically below. Unless stated otherwise, the radicals are each as defined above.

Process A

Scheme 1: Process A

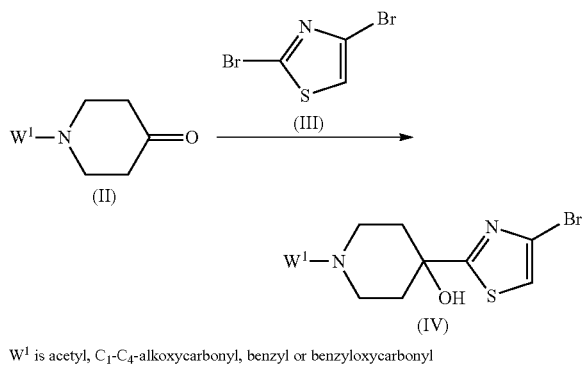

$W^1$ is acetyl, $C_1$-$C_4$-alkoxycarbonyl, benzyl or benzyloxycarbonyl

A compound of the general formula (IV) is obtained from a compound of the formula (III) by halogen-metal exchange and subsequent addition of a compound of the general formula (II) (see, for example, *Org. Lett.* 2004, 6, 3083-3085) (Scheme 1).

Process A is performed in the presence of a suitable organometallic compound. Preferred organometallic compounds are organolithium compounds (for example butyllithium) or Grignard reagents (for example isopropylmagnesium halide).

Process A is preferably performed using one or more diluents. Useful solvents are preferably aprotic solvents, for example dioxane, glyme, diethyl ether or tetrahydrofuran. Particular preference is given to the use of tetrahydrofuran.

In the performance of process A, the reaction temperatures can be varied within a relatively wide range. In the case of the halogen-metal exchange reactions, the temperatures employed are generally from −120° C. to +150° C., preferably temperatures from −120° C. to +60° C., most preferably −12° C. to 0° C. After the addition of compound (II), preference is given to working at −80° C. to +50° C.

To perform process A, generally 1 to 2 mol, preferably 1 mol, of the organometallic compound is used per mole of compound of the formula (III). The reaction time is 1 to 48 hours. The workup is effected by the customary methods. If necessary, the compounds are purified by recrystallization, distillation or chromatography, or they can optionally also be used in the next step without prior purification.

Process B

Scheme 2: Process B

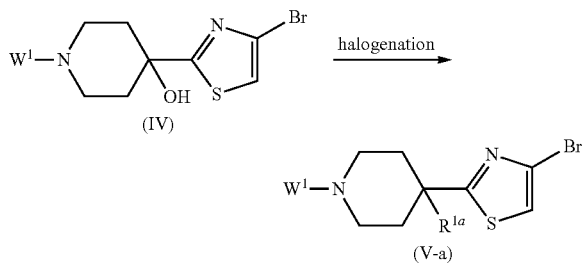

$W^1$ is acetyl, $C_1$-$C_4$-alkoxycarbonyl, benzyl or benzyloxycarbonyl
$R^{1a}$ is F, Cl, Br, I Process B describes the preparation of compounds of the structure (V-a) in which $R^{1a}$=F, Cl, Br and I by halogenation of compounds of the structure (IV) (see, for example, WO 2006/133216, WO 2004/108692, *J. Med. Chem.*, 1991, 34, 108-122, EP-A 0 796 846, *J. Antibiot.*, 1988, 41, 134-138, *Bioorg. Med. Chem. Lett.*, 2008, 18, 5209-5212, *Chem. Eur. J.*, 2004, 5640-5648, *Russ. J. Org. Chem.*, 2007, 50-55) (Scheme 2).

The solvents used may be all customary solvents which are inert under the reaction conditions, or the reaction can be performed in mixtures of two or more of these solvents. Preference is given to using the solvent dichloromethane.

The halogen source used may, for example, be diethylaminosulphur trifluoride, Selectfluor, Deoxofluor, thionyl chloride, $PBr_3$ and methanesulphonyl chloride.

The starting materials and the halogenating agent are used in equimolar amounts. The halogenating agent can also be used in excess. The reaction is normally performed at temperatures of −80° C. to +80° C. and preferably at 0° C. to +40° C., but it can also be performed at reflux temperature of the reaction mixture. The reaction time varies as a function of the scale of the reaction and the reaction temperature, but is generally between a few minutes and 48 hours.

After the reaction has ended, the compounds (V-a) are separated from the reaction mixture by one of the customary separation techniques. If necessary, the compounds are purified by recrystallization, distillation or chromatography, or they can optionally also be used in the next step without prior purification.

Process C

Scheme 3: Process C

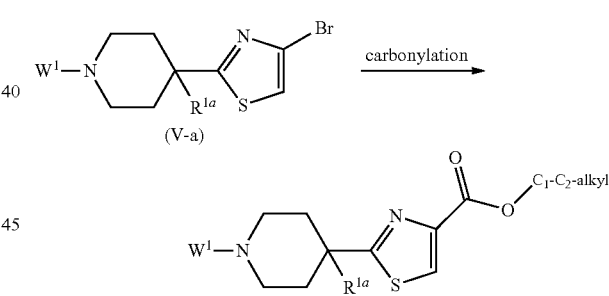

$W^1$ is acetyl, $C_1$-$C_4$-alkoxycarbonyl, benzyl or benzyloxycarbonyl
$R^{1a}$ is F, Cl, Br, I A compound of the general formula (VI-a) is obtained from a compound of the general formula (V-a) by metal-catalysed carbonylation (see, for example, *Synthetic Communications*, 1997, 515-520; *Journal of Organic Chemistry*, 2000, 7757-7763) (Scheme 3).

Process C is performed in the presence of a suitable catalyst and optionally in the presence of further cocatalysts (e.g. CuI) and of a base (e.g. triethylamine or $Cs_2CO_3$). The preferred catalysts are palladium catalysts (e.g. [(n-allyl)PdCl]$_2$, Pd(OAc)$_2$, PdCl$_2$(CH$_3$CN)$_2$, Pd(PPh$_3$)$_4$ or PdCl$_2$(PPh$_3$)$_2$).

Process C is preferably performed using one or more diluents. Useful diluents are preferably alcohols (e.g. methanol or ethanol).

The amount of catalyst used is 0.1-90 mol % based on the reactant; preference is given to using 1-30 mol % of the catalyst, based on the reactant. The reaction can be performed at elevated pressure (1-1000 bar) and preferably at pressure 1-5 bar. The reaction is normally carried out at temperatures of 0° C.-150° C. and preferably at room temperature, but it can also be carried out at reflux temperature of the reaction mixture. The reaction time varies as a function of the scale of the reaction and of the reaction temperature, but is generally between half an hour and 72 hours. The reaction is preferably performed at 80° C. and a CO pressure of 3 bar.

To perform process C, generally 0.5 to 10 mol, preferably 1 to 2 mol, of a base are used per mole of compound of the formula (V-a). The workup is effected by customary methods.

Compounds of the formula (VI-b) in which $R^{1b}$ is hydrogen are known and can be prepared from commercially available precursors by methods described in the literature (see, for example, WO 2009/037357).

Process D

Scheme 4: Process D

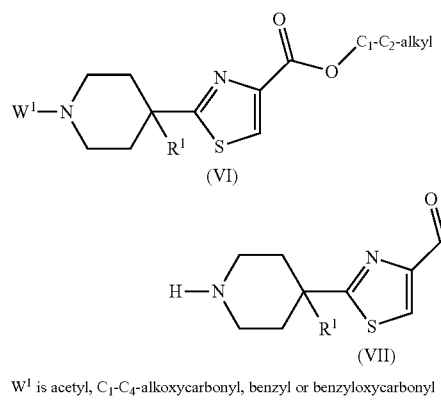

$W^1$ is acetyl, $C_1$-$C_4$-alkoxycarbonyl, benzyl or benzyloxycarbonyl

A compound of the formula (VI) is converted to a compound of the formula (VII) by suitable methods for removing protecting groups, which are described in the literature ("*Protective Groups in Organic Synthesis*"; Third Edition; 1999; 494-653, and literature cited therein) (Scheme 4).

tert-Butoxycarbonyl and benzyloxycarbonyl protecting groups can be removed in an acidic medium (for example with hydrochloric acid or trifluoroacetic acid). Acetyl protective groups can be removed under basic conditions (for example with potassium carbonate or caesium carbonate). Benzylic protective groups can be removed hydrogenolytically with hydrogen in the presence of a catalyst (for example palladium on activated carbon).

The solvents used may be all customary solvents which are inert under the reaction conditions, for example alcohols (e.g. methanol, ethanol, propanol), cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), nitriles (e.g. acetonitrile), carboxylic esters (e.g. ethyl acetate), amides (e.g. N,N-dimethylformamide, N,N-dimethylacetamide), dimethyl sulphoxide, 1,3-dimethyl-2-imidazolinone, water and acetic acid, or the reaction can be carried out in mixtures of two or more of these solvents.

Acids which can be used for this reaction, the deprotection of t-butoxycarbonyl and benzyloxycarbonyl groups, are, for example, trifluoroacetic acid, hydrochloric acid or other acids as described in the literature (for example "*Protective Groups in Organic Synthesis*"; Third Edition; 1999; pp. 494-653).

The reaction is normally performed at temperatures of 0° C. to +150° C. and preferably at room temperature, but it can also be performed at reflux temperature of the reaction mixture. The reaction time varies as a function of the scale of the reaction and of the reaction temperature, but is generally between half an hour and 72 hours.

After the reaction has ended, the compounds (VIII) are separated from the reaction mixture by one of the customary separation techniques. If necessary, the compounds are purified by recrystallization, distillation or chromatography, or can, if desired, also be used in the next step without prior purification. It is also possible to isolate the compound of the general formula (VII) as a salt, for example as a salt of hydrochloric acid or trifluoroacetic acid.

Process E

Scheme 5: Process E

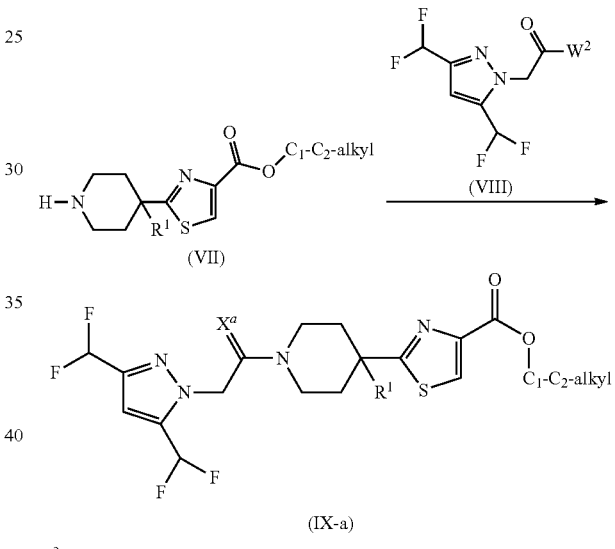

$W^2$ is chlorine or OH
$X^a$ is oxygen

A compound with the general formula (IX-a) can be synthesized analogously to the methods described in the literature (see, for example WO 07/147336), specifically by a coupling reaction of a compound with the general formula (VII) with a substrate of the general formula (VIII-a) ($W^{2a}$=chlorine), optionally in the presence of an acid scavenger/base (Scheme 5).

Compounds (VIII-a) ($W^{2a}$=chlorine) or (VIII-b) ($W^{2b}$=OH) can be prepared by processes described in the literature (see, for example, WO 2008/013622 and WO 2008/013925). It is also possible to prepare a substrate with the formula (VIII-a) ($W^{2a}$=chlorine) from the corresponding acid with the formula (VIII-b) ($W^{2b}$=OH) by chlorination using processes known from the literature (e.g. *Tetrahedron* 2005, 61, 10827-10852, and literature cited therein).

The solvents used may be all customary solvents which are inert under the reaction conditions, for example cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene) and nitriles (e.g. acetonitrile), or the reaction can be performed in mixtures of two or more of these solvents. The preferred solvents are tetrahydrofuran and dichloromethane.

At least one equivalent of an acid scavenger/of a base (for example Hünig's base, triethylamine or commercially available polymeric acid scavengers) is used, in relation to the starting material of the general formula (VII). If the starting material is a salt, at least two equivalents of the acid scavenger are required.

The reaction is normally performed at temperatures of 0° C. to 100° C. and preferably at 20° C. to 30° C., but it can also be performed at reflux temperature of the reaction mixture. The reaction time varies depending on the scale of the reaction and the reaction temperature, but is generally between a few minutes and 48 hours.

After the reaction has ended, the compounds (IX-a) are separated from the reaction mixture by one of the customary separation techniques. If necessary, the compounds are purified by recrystallization, distillation or chromatography, or they can optionally also be used in the next step without prior purification.

Alternatively, a compound of the formula (IX-a) can also be synthesized from the corresponding compound of the formula (VII) with a substrate of the formula (VIII-b) ($W^{2b}$=OH) in the presence of a coupling reagent (analogously to methods described in the literature, e.g. *Tetrahedron* 2005, 61, 10827-10852, and references cited therein).

Suitable coupling reagents are, for example, peptide coupling reagents (e.g. N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

If appropriate, a base, for example triethylamine or Hünig's base, can be used in the reaction.

The solvents used may be all customary solvents which are inert under the reaction conditions, for example alcohols (e.g. methanol, ethanol, propanol), cyclic and acyclic ethers (for example diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), nitriles (e.g. acetonitrile) and amides (e.g. N,N-dimethylformamide, N,N-dimethylacetamide), or the reaction can be carried out in mixtures of two or more of these solvents. The preferred solvent is dichloromethane.

The reaction is normally performed at temperatures of 0° C.-100° C. and preferably at 0° C.-30° C., but it can also be carried out at reflux temperature of the reaction mixture. The reaction time varies depending on the scale of the reaction and the reaction temperature, but is generally between a few minutes and 48 hours.

After the reaction has ended, the compounds (IX-a) are separated from the reaction mixture by one of the customary separation techniques. If necessary, the compounds are purified by recrystallization, distillation or chromatography, or they can optionally also be used in the next step without prior purification.

Process F

Scheme 6: Process F

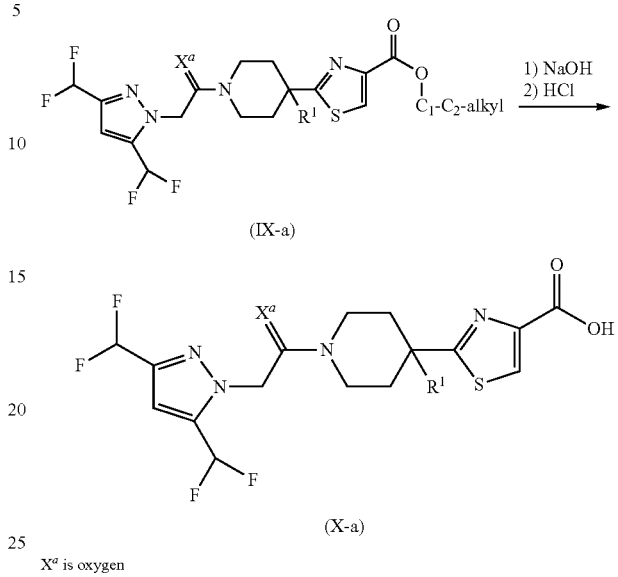

$X^a$ is oxygen

The carboxylic acid of the formula (X-a) can be prepared by hydrolysing the corresponding $C_1$-$C_2$-alkyl ester of the formula (IX-a). For example, the method described in WO 2007/014290 can be used (Scheme 6).

The solvents used may be all customary solvents which are inert under the reaction conditions, for example alcohols (e.g. methanol, ethanol, propanol), cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride) and halogenated aromatic hydrocarbons (e.g. chlorobenzene, dichlorobenzene), or the reaction can be performed in mixtures of two or more of these solvents.

Suitable alkali metal hydroxides are, for example, LiOH, NaOH or KOH, usually in the presence of water together with a cosolvent, preferably THF and/or methanol, to simplify dissolution of the ester. The starting material and the alkali metal hydroxide are used in equimolar amounts, but the alkali metal hydroxide may optionally also be used in excess. The carboxylate salt formed is converted to the free acid by treatment with a slight excess of mineral acids, for example hydrochloric acid or sulphuric acid.

The reaction is normally performed at temperatures of 0° C.-60° C., but it can also be carried out at reflux temperature of the reaction mixture. The reaction time varies depending on the scale of the reaction and the reaction temperature, but is generally between a few minutes and 48 hours.

After the reaction has ended, the compounds (X-a) are separated from the reaction mixture by one of the customary separation techniques. If necessary, the compounds are purified by recrystallization, distillation or chromatography.

Process G

Scheme 7: Process G

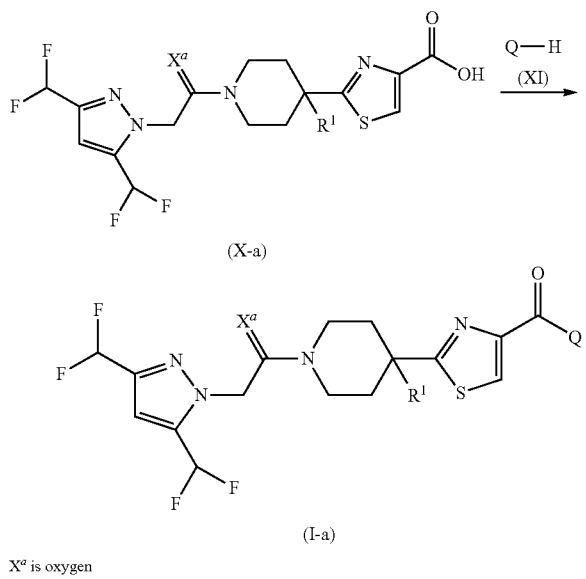

(X-a)

(I-a)

$X^a$ is oxygen

A compound with the formula (I-a) can be synthesized from the corresponding compound of the formula (X-a) with a substrate of the formula (XI) in the presence of a coupling reagent (analogously to methods described in the literature, e.g. *Tetrahedron* 2005, 61, 10827-10852, and references cited therein).

Suitable coupling reagents are, for example, peptide coupling reagents (for instance N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

If appropriate, a base, for example triethylamine or Hünig's base, can be used in the reaction.

The preferred solvents are N,N-dimethylformamide and dichloromethane.

The reaction is normally performed at temperatures of 0° C.-100° C. and preferably at 0° C.-30° C., but it can also be carried out at reflux temperature of the reaction mixture. The reaction time varies depending on the scale of the reaction and the reaction temperature, but is generally between a few minutes and 48 hours.

After the reaction has ended, the compounds (I-a) are removed from the reaction mixture by one of the customary separation techniques. If necessary, the compounds are purified by recrystallization, distillation or chromatography, or they can optionally also be used in the next step without prior purification.

Alternatively, a compound of the formula (I-a) can also be synthesized proceeding from the compound of the formula (X-a) by a two-stage transformation (using processes known from the literature, e.g. *Tetrahedron* 2005, 61, 10827-10852, and literature cited therein), optionally in the presence of an acid scavenger/base. Typically, a compound of the formula (X-a) is first converted to the corresponding acid halide or sulphonate, followed by a coupling reaction with a substrate of the formula (XI).

Substrates with the general formula (XI) are commercially available or preparable by processes described in the literature (see, for example, "The Chemistry of Functional groups"; "The Chemistry of the Thiol Group"; John Wiley & Sons, 1974, 163-269, and references cited therein; "The Chemistry of Functional groups"; "Supplement F2: The Chemistry of amino, nitroso, nitro and related groups"; John Wiley & Sons, and the references cited therein; "Science of Synthesis"; "Alcohols", Volume 36, Thieme, 2008 and the references cited therein; "Science of Synthesis"; "Amines and Ammonium Salts", Volume 40a, Thieme, 2008, and the references cited therein).

In the performance of process G according to the invention, it is possible to use all customary solvents which are inert under the reaction conditions, for example alcohols (e.g. methanol, ethanol, propanol), cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene) and nitriles (e.g. acetonitrile), or the reaction can be performed in mixtures of two or more of these solvents. The preferred solvents are tetrahydrofuran and dichloromethane.

At least one equivalent of an acid scavenger/a base (for example Hünig's base, triethylamine or commercially available polymeric acid scavengers) is used, in relation to the starting material of the general formula (XI). If the starting material is a salt, at least two equivalents of the acid scavenger are required.

The reaction is normally performed at temperatures of 0° C.-100° C. and preferably at 20° C.-30° C., but it can also be carried out at reflux temperature of the reaction mixture. The reaction time varies depending on the scale of the reaction and the reaction temperature, but is generally between a few minutes and 48 hours.

After the reaction has ended, the compounds (I-a) are removed from the reaction mixture by one of the customary separation techniques. If necessary, the compounds are purified by recrystallization, distillation or chromatography, or they can optionally also be used in the next step without prior purification.

Process H

Scheme 8: Process H

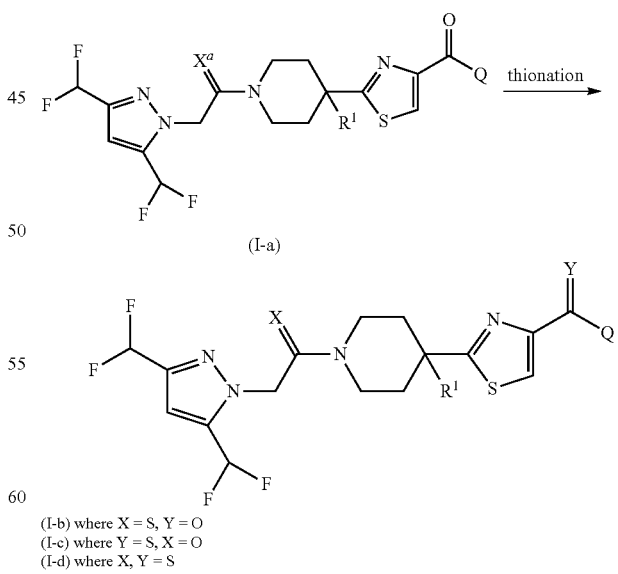

(I-a)

(I-b) where X = S, Y = O
(I-c) where Y = S, X = O
(I-d) where X, Y = S

One means of preparing compounds of the formula (I-b), (I-c) or (I-d) from corresponding compounds (I-a) is shown in Scheme 8.

The solvents used may be all customary solvents which are inert under the reaction conditions, for example alcohols (e.g. methanol, ethanol, propanol), cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), nitriles (e.g. acetonitrile), carboxylic esters (e.g. ethyl acetate) and amides (e.g. N,N-dimethylformamide, N,N-dimethylacetamide), and the reaction can be carried out in mixtures of two or more of these solvents. The preferred solvents are chloroform and 1,2-dimethoxyethane.

Suitable thionating reagents are, for example, Lawesson's reagent (see *Tetrahedron* 1986, 42, 6555-6564, *Tetrahedron Lett.* 1993, 46, 7459-7462) and phosphorus pentasulphide.

The thionating reagent is used in excess (more than two equivalents) in relation to the starting material.

The reaction is normally performed at temperatures of 0° C.-150° C. and preferably at 0° C.-100° C., but it can also be carried out at reflux temperature of the reaction mixture. The reaction time varies depending on the scale of the reaction and the reaction temperature, but is generally between a few minutes and 48 hours.

The reaction proceeds non-selectively in the case of an excess of thionating reagent. This gives a mixture of the products (I-b), (I-c) and (I-d), which, after the reaction has ended, are separated by one of the customary separation techniques, e.g. chromatography.

The present invention further relates to a crop protection composition for controlling unwanted fungi, comprising at least one of the bis(difluoromethyl)pyrazole derivatives of the formula (I). These are preferably fungicidal compositions which comprise agriculturally suitable auxiliaries, solvents, carriers, surfactants or extenders.

The invention also relates to a method for controlling unwanted microorganisms, characterized in that, in accordance with the invention, bis(difluoromethyl)pyrazole derivatives of the formula (I) are applied to the phytopathogenic fungi and/or their habitat.

According to the invention, a carrier is a natural or synthetic organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and ground natural minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral and vegetable oils and derivatives of these. Mixtures of such carriers can likewise be used. Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Suitable liquefied gaseous extenders or carriers are liquids which are gaseous at ambient temperature and under atmospheric pressure, for example aerosol propellants, such as halohydrocarbons, and also butane, propane, nitrogen and carbon dioxide.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

If the extender used is water, it is also possible to use, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

The inventive compositions may additionally comprise further components, for example surfactants. Useful surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkylsulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 per cent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

If appropriate, it is also possible for other additional components to be present, for example protective colloids, binders, adhesives, thickeners, thixotropic substances, penetrants, stabilizers, sequestering agents, complex formers. In general, the active ingredients can be combined with any solid or liquid additive commonly used for formulation purposes.

The formulations generally contain between 0.05 and 99% by weight, 0.01 and 98% by weight, preferably between 0.1 and 95% by weight, more preferably between 0.5 and 90% of active ingredient, most preferably between 10 and 70 per cent by weight.

The inventive active ingredients or compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active ingredient, and also microencapsulations in polymeric substances and in coating materials for seed, and also ULV cold-fogging and warm-fogging formulations.

The formulations mentioned can be prepared in a manner known per se, for example by mixing the active ingredients with at least one customary extender, solvent or diluent, emulsifier, dispersant, and/or binder or fixative, wetting agent, water repellent, if appropriate desiccants and UV stabilizers and, if appropriate, dyes and pigments, defoamers, preservatives, secondary thickeners, adhesives, gibberellins and also further processing auxiliaries.

The inventive compositions include not only formulations which are already ready for use and can be applied with a suitable apparatus to the plant or the seed, but also commercial concentrates which have to be diluted with water prior to use.

The inventive active ingredients can be present as such or in their (commercial) formulations and in the use forms, prepared from these formulations, as a mixture with other (known) active ingredients, such as insecticides, attractants, sterilants, bactericides, acaricides, nematicides, fungicides, growth regulators, herbicides, fertilizers, safeners and/or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

The invention further comprises a method for treating seed.

The invention further relates to seed which has been treated by one of the methods described in the previous paragraph. The inventive seeds are employed in methods for the protection of seed from unwanted fungi. In these methods, seed treated with at least one inventive active ingredient is used.

The inventive active ingredients or compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner. Thus, it is desirable to develop methods for protecting the seed and the germinating plant which dispense with, or at least reduce considerably, the additional deployment of crop protection compositions after sowing or after emergence of the plants. It is also desirable to optimize the amount of the active ingredient used so as to provide the best possible protection for the seed and the germinating plant from attack by phytopathogenic fungi, but without damaging the plant itself by the active ingredient employed. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention also relates to the use of the inventive compositions for treating seed for protecting the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions not only protects the seed itself, but also the resulting plants after emergence, from phytopathogenic fungi. In this way, the immediate treatment of the crop at the time of sowing or shortly thereafter can be dispensed with.

It is also considered to be advantageous that the inventive active ingredients or compositions can especially also be used with transgenic seed, in which case the plant growing from this seed is capable of expressing a protein which acts against pests. By treatment of such seed with the inventive active ingredients or compositions, merely by the expression of the protein, for example an insecticidal protein, certain pests may be controlled. Surprisingly, a further synergistic effect may be observed here, which additionally increases the effectiveness for protection against attack by pests.

The inventive compositions are suitable for protecting seed of any plant variety which is used in agriculture, in greenhouses, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular importance.

As also described below, the treatment of transgenic seed with the inventive active ingredients or compositions is of particular importance. This relates to the seed of plants containing at least one heterologous gene which enables the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. The heterologous gene more preferably originates from *Bacillus thuringiensis*.

Within the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, has been treated, for example, with water and then dried again.

When treating the seed, care must generally be taken that the amount of the inventive composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for treating seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active ingredients usable in accordance with the invention can be converted to the customary seed dressing formulations, such as solutions, emulsions, suspensions, powders, foams, slurries or other coating materials for seed, and also ULV formulations.

These formulations are prepared in a known manner, by mixing the active ingredients with customary additives, for example customary extenders and also solvents or diluents, dyes, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Suitable wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Stickers which may be present in the seed dressing formulations usable in accordance with the invention are all customary binders usable in seed dressing products. Preferred examples include polyvinylpyrrolidone, polyvinyl acetate, polyvinyl alcohol and tylose.

Gibberellins which may be present in the seed dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of Crop Protection Compositions and Pesticides], vol. 2, Springer Verlag, 1970, p. 401-412).

The seed dressing formulations usable in accordance with the invention can be used, either directly or after previously having been diluted with water, for the treatment of a wide range of different seed, including the seed of transgenic plants. In this context, additional synergistic effects may also occur in interaction with the substances formed by expression.

For the treatment of seed with the seed dressing formulations usable in accordance with the invention or with the preparations prepared therefrom by addition of water, useful equipment is all mixing units usable customarily for seed dressing. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

The inventive active ingredients or compositions have a potent fungicidal activity and can be used for controlling unwanted fungi in crop protection and in the protection of materials.

The inventive bis(difluoromethyl)pyrazole derivatives can be used in crop protection for controlling *Plasmodiophoromycetes, Oomycetes, Chytridiomycetes, Zygomycetes, Ascomycetes, Basidiomycetes* and *Deuteromycetes*.

The inventive fungicidal compositions can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The inventive compositions for controlling phytopathogenic fungi in crop protection comprise an effective but non-phytotoxic amount of the inventive active ingredients. An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

The fact that the active ingredients are well tolerated by plants at the concentrations required for controlling plant diseases allows the treatment of above-ground parts of plants, of propagation stock and seeds, and of the soil.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant varieties which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits, seeds, roots, tubers and rhizomes. Parts of plants also include harvested plants and vegetative and generative propagation material, for example seedlings, tubers, rhizomes, cuttings and seeds.

The inventive active ingredients, when they are well tolerated by plants, have favourable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and also against all or some stages of development.

Plants which can be treated in accordance with the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana plants and banana plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leeks, onions), *Papilionaceae* sp. (for example peas); major crop plants such as *Gramineae* sp. (for example maize, turf, cereals such as wheat, rye, rice, barley, oats, millet and triticale), *Poaceae* sp. (for example sugar cane), *Asteraceae* sp. (for example sunflower), *Brassicaceae* sp. (for example white cabbage, red cabbage, broccoli, cauliflower, Brussels sprouts, pak Choi, kohlrabi, radishes, and also oilseed rape, mustard, horseradish and cress), *Fabacae* sp. (for example beans, peanuts), *Papilionaceae* sp. (for example soya beans), *Solanaceae* sp. (for example potatoes), *Chenopodiaceae* sp. (for example sugar beet, fodder beet, Swiss chard, beetroot); useful plants and ornamental plants in gardens and forests; and in each case genetically modified types of these plants.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above. Particularly preferably, plants of the plant cultivars which are in each case commercially available or in use are treated in accordance with the invention. Plant cultivars are to be understood as meaning plants having new properties ("traits") and which have been obtained by conventional breeding, by mutagenesis or by recombinant DNA techniques. They can be cultivars, varieties, bio- or genotypes.

The inventive treatment method can be used for the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Possible are thus, for example, the following effects which exceed the effects which were actually to be expected: reduced application rates and/or a widening of the activity spectrum and/or an increase in the activity of the active ingredients and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products.

At certain application rates, the inventive active ingredient combinations may also have a fortifying effect in plants. They are therefore suitable for mobilizing the defence system of the plant against attack by unwanted phytopathogenic fungi and/or microorganisms and/or viruses. This may be one of the reasons for the enhanced activity of the inventive combinations, for example against fungi. Plant-fortifying (resistance-inducing) substances shall be understood to mean, in the present context, also those substances or combinations of substances which are capable of stimulating the defence system of plants in such a way that, when subsequently inoculated with unwanted phytopathogenic fungi, the plants treated display a substantial degree of resistance to these unwanted phytopathogenic fungi. The inventive substances can therefore be employed for protection of plants from attack by the pathogens mentioned within a certain period of time after the treatment. The period within which protection is achieved generally extends for from 1 to 10 days, preferably 1 to 7 days, after the treatment of the plants with the active ingredients.

Plants and plant varieties which are preferably treated in accordance with the invention include all plants which have genetic material which imparts particularly advantageous, useful traits to these plants (whether obtained by breeding and/or biotechnological means).

Plants and plant varieties which are also preferably treated in accordance with the invention are resistant against one or more biotic stress factors, i.e. said plants have a better defence against animal and microbial pests, such as against nematodes, insects, mites, phytopathogenic fungi, bacteria, viruses and/or viroids.

Plants and plant varieties which may also be treated in accordance with the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated in accordance with the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated in accordance with the invention are hybrid plants that already express the characteristics of heterosis, or hybrid effect, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated in accordance with the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an Eleusine EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is converted to homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio) benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides.

The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding.

Plants or plant varieties (obtained by plant biotechnology methods such as genetic engineering) which may also be treated in accordance with the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins listed online at:
   http://www.lifesci.sussex.ac.uk/Home/Neil_Crickmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or
3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or
4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR 604;
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, e.g. proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated in accordance with the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants;
b. plants which contain a stress tolerance-enhancing transgene capable of reducing the expression and/or the activity of the PARG-encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated in accordance with the invention show altered quantity, quality and/or storage stability of the harvested product and/or altered properties of specific ingredients of the harvested product such as, for example:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications.
2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.
3) Transgenic plants which produce hyaluronan.

Plants or plant varieties (obtained by plant biotechnology methods such as genetic engineering) which may also be treated in accordance with the invention are plants, such as cotton plants, with altered fibre characteristics. Such plants can be obtained by genetic transformation, or by selection of plants containing a mutation imparting such altered fibre characteristics and include:

a) plants, such as cotton plants, which contain an altered form of cellulose synthase genes;

b) plants, such as cotton plants, which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;
e) plants, such as cotton plants, wherein the timing of the plasmodesmatal gating at the basis of the fibre cell is altered, for example through downregulation of fibre-selective 13-1,3-glucanase;
f) plants, such as cotton plants, which have fibres with altered reactivity, for example through the expression of the N-acetylglucosaminetransferase gene including nodC and chitin synthase genes.

Plants or plant cultivars (obtained by plant biotechnology methods such as genetic engineering) which may also be treated in accordance with the invention are plants, such as oilseed rape or related *Brassica* plants, with altered oil profile characteristics. Such plants can be obtained by genetic transformation or by selection of plants containing a mutation imparting such altered oil characteristics and include:
a) plants, such as oilseed rape plants, which produce oil having a high oleic acid content;
b) plants, such as oilseed rape plants, which produce oil having a low linolenic acid content;
c) plants, such as oilseed rape plants, which produce oil having a low level of saturated fatty acids.

Particularly useful transgenic plants which can be treated in accordance with the invention are plants which comprise one or more genes which encode one or more toxins and are the transgenic plants available under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize) Herbicide-resistant plants (plants bred in a conventional manner for herbicide tolerance) which may be mentioned include the varieties sold under the name Clearfield® (for example maize).

Particularly useful transgenic plants which can be treated in accordance with the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

Moreover, in the protection of materials, the inventive active ingredients or compositions can be employed for protecting industrial materials against attack and destruction by unwanted microorganisms, for example fungi.

Industrial materials in the present context are understood as meaning non-living materials which have been prepared for use in industry. For example, industrial materials which are intended to be protected by inventive active ingredients from fungal change or destruction can be adhesives, sizes, paper, wallpaper and board, textiles, carpets, leather, wood, paints and plastic articles, cooling lubricants and other materials which can be infected with, or destroyed by, microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood. The inventive active ingredients or compositions may prevent adverse effects, such as rotting, decay, discoloration, decoloration or formation of mould. Moreover, the inventive compounds can be used to protect objects which come into contact with saltwater or brackish water, especially hulls, screens, nets, buildings, moorings and signalling systems, from fouling.

The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre) drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mould.

Non-limiting examples of pathogens of fungal diseases which can be treated in accordance with the invention include:

diseases caused by powdery mildew pathogens, for example Blumeria species, for example *Blumeria graminis; Podosphaera* species, for example *Podosphaera leucotricha; Sphaerotheca* species, for example *Sphaerotheca fuliginea; Uncinula* species, for example *Uncinula necator;* diseases caused by rust disease pathogens, for example Gymnosporangium species, for example *Gymnosporangium sabinae; Hemileia* species, for example *Hemileia vastatrix; Phakopsora* species, for example *Phakopsora pachyrhizi* and *Phakopsora meibomiae; Puccinia* species, for example *Puccinia recondita* or *Puccinia triticina; Uromyces* species, for example *Uromyces appendiculatus;* diseases caused by pathogens from the group of the Oomycetes, for example *Bremia* species, for example *Bremia lactucae; Peronospora* species, for example *Peronospora pisi* or *P. brassicae; Phytophthora* species, for example *Phytophthora infestans; Plasmopara* species, for example *Plasmopara viticola; Pseudoperonospora* species, for example *Pseudoperonospora humuli* or *Pseudoperonospora cubensis; Pythium* species, for example *Pythium ultimum;* leaf blotch diseases and leaf wilt diseases caused, for example, by *Alternaria* species, for example *Alternaria solani; Cercospora* species, for example *Cercospora beticola; Cladiosporium* species, for example *Cladiosporium cucumerinum; Cochliobolus* species, for example *Cochliobolus sativus* (conidia form: *Drechslera*, syn: *Helminthosporium); Colletotrichum* species, for example *Colletotrichum lindemuthanium; cycloconium* species, for example *cycloconium oleaginum; Diaporthe* species, for example *Diaporthe citri; Elsinoe* species, for example *Elsinoe fawcettii; Gloeosporium* species, for example *Gloeosporium laeticolor; Glomerella* species, for example *Glomerella cin-* gulata; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola* and *M. fijiensis*; *Phaeosphaeria* species, for example *Phaeosphaeria nodorum*; *Pyrenophora* species, for example *Pyrenophora teres*; *Ramularia* species, for example *Ramularia collo-cygni*; *Rhynchosporium* species, for example *Rhynchosporium secalis*; *Septoria* species, for example *Septoria apii*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*;

*Verticilium* species, for example *Verticilium alboatrum*;

seed- and soil-borne rot and wilt diseases, and also diseases of seedlings, caused, for example, by *Fusarium* species, for example *Fusarium culmorum*; *Phytophthora* species, for example *Phytophthora cactorum*; *Pythium* species, for example *Pythium ultimum*; *Rhizoctonia* species, for example *Rhizoctonia solani*; *Sclerotium* species, for example *Sclerotium rolfsii*;

cancerous diseases, galls and witches' broom caused, for example, by Nectria species, for example *Nectria galligena*;

wilt diseases caused, for example, by *Monilinia* species, for example *Monilinia laxa*;

deformations of leaves, flowers and fruits caused, for example, by *Taphrina* species, for example *Taphrina deformans*;

degenerative diseases of woody plants caused, for example, by *Esca* species, for example *Phaeomoniella chlamydospora* and *Phaeoacremonium aleophilum* and *Fomitiporia mediterranea*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

Preference is given to controlling the following diseases of soya beans:

Fungal diseases on leaves, stems, pods and seeds caused, for example, by alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Organisms which can bring about degradation or modification of the industrial materials include fungi. The inventive active ingredients preferably act against fungi, in particular moulds, wood-discoloring and wood-destroying fungi (Basidiomycetes). Examples include fungi of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*.

In addition, the inventive active ingredients also have very good antimycotic activity. They have a very broad antimycotic activity spectrum, in particular against dermatophytes and yeasts, moulds and diphasic fungi, (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and audouinii. The list of these fungi by no means constitutes a restriction of the mycotic spectrum covered, and is merely of illustrative character.

When using the inventive active ingredients as fungicides, the application rates can be varied within a relatively wide range, depending on the kind of application. The application rate of the inventive active ingredients is when treating plant parts, for example leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rockwool or perlite are used);

when treating seed: from 2 to 200 g per 100 kg of seed, preferably from 3 to 150 g per 100 kg of seed, more preferably from 2.5 to 25 g per 100 kg of seed, most preferably from 2.5 to 12.5 g per 100 kg of seed;

when treating the soil: from 0.1 to 10 000 g/ha, preferably from 1 to 5000 g/ha.

These application rates are mentioned merely by way of example and are not limiting for the purposes of the invention.

The inventive active ingredients or compositions can thus be used to protect plants from attack by the pathogens mentioned for a certain period of time after treatment. The period for which protection is provided extends generally for 1 to 28 days, preferably for 1 to 14 days, more preferably for 1 to 10 days, most preferably for 1 to 7 days, after the treatment of the plants with the active ingredients, or for up to 200 days after a seed treatment.

In addition, the inventive treatment can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *Fusarium acuminatum, F. avenaceum, F. crookwellense, F. culmorum, F. graminearum (Gibberella zeae), F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec., inter alia.

The plants listed can be treated in accordance with the invention in a particularly advantageous manner with the bis(difluoromethyl)pyrazole derivatives of the formula (I) or the inventive compositions. The preferred ranges stated above for the active ingredients or compositions also apply to the treatment of these plants. Particular emphasis is given to the treatment of plants with the compounds or compositions specifically mentioned in the present text.

The preparation and the use of the inventive active ingredients of the formula (I) is illustrated by the examples below. However, the invention is not limited to these examples.

General Note:

Unless stated otherwise, all chromatographic purification and separation steps were carried out on silica gel and with a solvent gradient of 0:100 ethyl acetate/cyclohexane to 100:0 ethyl acetate/hexane.

Preparation of Compounds of the Formula (I)

Process A tert-Butyl 4-(4-bromo-1,3-thiazol-2-yl)-4-hydroxypiperidine-1-carboxylate (IV-1)

To a solution of 2,4-dibromo-1,3-thiazole (8.8 g) in dichloromethane (180 ml) was added dropwise, at −78° C. under an argon atmosphere, n-butyllithium (1.6 M in tetrahydrofuran, 25 ml). The reaction mixture was stirred at −78° C. for 20 minutes and then tert-butyl 4-oxopiperidine-1-carboxylate was added. The mixture was stirred at room temperature for 30 minutes. The reaction mixture was subsequently admixed with saturated ammonium chloride solution at −30° C. and the aqueous phase was removed. After the aqueous phase had been extracted with dichloromethane, the combined organic phases were dried over sodium sulphate and concentrated under reduced pressure. The residue was purified chromatographically. This gave tert-butyl 4-(4-bromo-1,3-thiazol-2-yl)-4-hydroxypiperidine-1-carboxylate (15.3 g).

$^1$H NMR (DMSO-d$_6$): $\delta_{ppm}$: 1.43 (s, 9H), 1.70 (d, 2H), 1.88 (ddd, 2H), 3.11 (bs, 2H), 3.83 (d, 2H), 6.31 (s, 1H), 7.72 (s, 1H)

log P (HCOOH): 2.74

MS (ESI): 363 and 365 ([M+H]$^+$)

Process B tert-Butyl 4-(4-bromo-1,3-thiazol-2-yl)-4-fluoropiperidine-1-carboxylate (Va-1)

tert-Butyl 4-(4-bromo-1,3-thiazol-2-yl)-4-hydroxypiperidine-1-carboxylate (17.7 g) was initially charged under an argon atmosphere at 0° C. in dichloromethane in a polyethylene flask, and diethylaminosulphur trifluoride (DAST) (7.08 ml) was added dropwise. The cooling was removed. After the mixture had been stirred overnight, the reaction mixture was extracted with saturated aqueous sodium hydrogencarbonate solution and then extracted with dichloromethane. The organic extracts were dried over sodium sulphate and concentrated under reduced pressure. The residue was purified by chromatography. This gave tert-butyl 4-(4-bromo-1,3-thiazol-2-yl)-4-fluoropiperidine-1-carboxylate (18.0 g).

$^1$H NMR (DMSO-d$_6$): $\delta_{ppm}$: 1.42 (s, 9H), 2.13-2.00 (m, 4H), 3.14 (bs, 2H), 3.95-3.87 (m, 2H), 7.95 (s, 1H)

log P (HCOOH): 3.94

MS (ESI): 309 and 311 ([M-C(CH$_3$)$_3$+2H]$^+$)

Process C tert-Butyl 4-[4-(ethoxycarbonyl)-1,3-thiazol-2-yl]-4-fluoropiperidine-1-carboxylate (VIa-1)

tert-Butyl 4-(4-bromo-1,3-thiazol-2-yl)-4-fluoropiperidine-1-carboxylate (29 g) was dissolved in ethanol (150 ml) and stirred at 70° C. under 3 bar of CO for 48 hours in the presence of PdCl$_2$(PPh)$_2$ (2.79 g) and triethylamine (77 ml). The catalyst was removed by filtration through Celite and the mixture was concentrated under reduced pressure. Purification by chromatography gave tert-butyl 4-[4-(ethoxycarbonyl)-1,3-thiazol-2-yl]-4-fluoropiperidine-1-carboxylate (380 mg).

log P (pH2.7): 3.47

$^1$H NMR (DMSO-d$_6$, 400 MHz): $\delta_{ppm}$: 1.31 (t, 3H), 1.42 (s, 9H), 2.00-2.20 (m, 4H), 3.13 (bs, 2H), 3.90-3.98 (m, 2H), 4.32 (q, 2H), 8.60 (s, 1H)

MS (ESI): 303 ([M-C(CH$_3$)$_3$+2H]$^+$)

Process D

4-[4-(Ethoxycarbonyl)-1,3-thiazol-2-yl]-4-fluoropiperidinium chloride (VII-1)

To tent-butyl 4-[4-(ethoxycarbonyl)-1,3-thiazol-2-yl]-4-fluoropiperidine-1-carboxylate (8.80 g) was added, under an argon atmosphere at 0° C., a solution of hydrogen chloride in dioxane (4 M, 92 ml). The mixture was stirred at 0° C. and then slowly warmed to room temperature. After stirring for 24 hours, the excess acid and the solvent were removed under reduced pressure. This gave 4-[4-(ethoxycarbonyl)-1,3-thiazol-2-yl]-4-fluoropiperidinium chloride (7.70 g).

log P (pH2.7): 0.39

$^1$H NMR (DMSO-d$_6$, 400 MHz): δ$_{ppm}$: 1.31 (t, 3H), 2.30-2.60 (m, 4H), 3.10-3.21 (m, 2H), 3.32-3.42 (2H), 4.32 (q, 2H), 8.64 (s, 1H), 9.20 (bs, 1H)

MS (ESI): 259 ([MCl]$^+$)

Process E

Ethyl 2-(1-{[3,5-bis(difluoromethyl)-1H-pyrazol-1-yl]acetyl}-4-fluoropiperidin-4-yl)-1,3-thiazole-4-carboxylate (IXa-1)

To a solution of [3,5-bis(difluoromethyl)-1H-pyrazol-1-yl]acetic acid (230 mg) in dichloromethane (5 ml) were added, at 0° C., oxalyl chloride (0.89 ml) and one drop of N,N-dimethylformamide. The reaction mixture was stirred at room temperature for 24 hours. The solvent and the excess reagent were removed under reduced pressure. The solid residue was then dissolved again in dichloromethane and added dropwise at 0° C. to a solution of 4-[4-(ethoxycarbonyl)-1,3-thiazol-2-yl]-4-fluoropiperidinium chloride (767 mg) and N,N-diisopropylethylamine (1.8 ml) in dichloromethane (5 ml). After the mixture had been stirred for 2 hours, concentrated ammonium chloride solution was added to the reaction solution, and the aqueous phase was removed and extracted with ethyl acetate. The combined organic phases were dried over anhydrous sodium sulphate and concentrated. This gave ethyl 2-(1-{[3,5-bis(difluoromethyl)-1H-pyrazol-1-yl]acetyl}-4-fluoropiperidin-4-yl)-1,3-thiazole-4-carboxylate (1.02 g).

log P (pH2.7): 2.82

$^1$H NMR (DMSO-d$_6$, 400 MHz): δ$_{ppm}$: 1.31 (t, 3H), 2.05-2.21 (m, 3H), 2.38-2.51 (m, 1H), 3.03-3.08 (m, 1H), 3.42-3.48 (m, 1H), 3.90-3.95 (m, 1H), 4.27-4.33 (m, 3H), 5.42 (d, 1H), 5.53 (d, 1H), 6.93 (s, 1H), 7.05 (t, 1H), 7.20 (t, 1H), 8.64 (s, 1H)

MS (ESI): 467 ([M+H]$^+$)

Process F 2-(1-{[3,5-bis(Difluoromethyl)-1H-pyrazol-1-yl]acetyl}-4-fluoropiperidin-4-yl)-1,3-thiazole-4-carboxylic acid (Xa-1)

To a solution of ethyl 2-(1-{[3,5-bis(difluoromethyl)-1H-pyrazol-1-yl]acetyl}-4-fluoropiperidin-4-yl)-1,3-thiazole-4-carboxylate (300 mg) in tetrahydrofuran (3 ml) and water (1 ml) was added, at room temperature, lithium hydroxide monohydrate (40 mg). The mixture was stirred at room temperature for 3 hours, and then ice-cold 1N HCl solution was added. The aqueous phase was extracted with ethyl acetate and then the combined organic phases were dried over sodium sulphate. The solids were filtered off and the solvent was distilled off. This gave 2-(1-{[3,5-bis(difluoromethyl)-1H-pyrazol-1-yl]acetyl}-4-fluoropiperidin-4-yl)-1,3-thiazole-4-carboxylic acid (230 mg).

log P (pH2.7): 1.96

$^1$H NMR (DMSO-d$_6$, 400 MHz): δ$_{ppm}$: 2.00-2.60 (m, 4H), 3.02-3.13 (m, 1H), 3.40-3.51 (m, 1H), 3.86-3.99 (m, 1H), 4.22-4.30 (m, 1H), 5.40 (d, 1H), 5.50 (d, 1H), 6.91 (s, 1H), 7.03 (t, 1H), 7.19 (t, 1H), 8.54 (s, 1H), 13.10 (bs, 1H)

MS (ESI): 439 ([M+H]$^+$)

Process G (±)-2-(1-{[3,5-bis(Difluoromethyl)-1H-pyrazol-1-yl]acetyl}-4-fluoropiperidin-4-yl)-N-methyl-N-(1,2,3,4-tetrahydronaphthalen-1-yl)-1,3-thiazole-4-carboxamide (Ia-4)

2-(1-{[3,5-bis(Difluoromethyl)-1H-pyrazol-1-yl]acetyl}-4-fluoropiperidin-4-yl)-1,3-thiazole-4-carboxylic acid (2 g), (±)-N-methyl-1,2,3,4-tetrahydronaphthalene-1-amine (736 mg) and Hünig's base (1.59 ml) were dissolved in dichloromethane (20 ml), and then bromotrispyrrolidino-phosphonium hexafluorophosphate (2.34 g) was added. The reaction mixture was stirred at room temperature overnight. After the solvent had been removed under reduced pressure, the residue was purified by chromatography. This gave (±)-2-(1-{[3,5-bis(difluoromethyl)-1H-pyrazol-1-yl]acetyl}-4-fluoropiperidin-4-yl)-N-methyl-N-(1,2,3,4-tetrahydronaphthalen-1-yl)-1,3-thiazole-4-carboxamide (1.70 g).

log P (pH2.7): 3.56

$^1$H NMR (DMSO-d$_6$, 400 MHz): δ$_{ppm}$: 1.50-2.85 (m, 13H), 3.10-3.25 (m, 1H), 3.40-3.55 (m, 1H), 3.80-3.94 (m, 1H), 4.03-4.28 (m, 1H), 5.17-5.53 and 5.77-5.83 (m, 3H), 6.90 (s, 1H), 7.00-7.40 (m, 5H), 8.28 and 8.32 (s, 1H)

MS (ESI): 439 ([M+H]$^+$)

(−)-2-(1-{[3,5-bis(Difluoromethyl)-1H-pyrazol-1-yl]acetyl}-4-fluoropiperidin-4-yl)-N-methyl-N-(1,2,3,4-tetrahydronaphthalen-1-yl)-1,3-thiazole-4-carboxamide (I-5) and (+)-2-(1-{[3,5-bis(difluoromethyl)-1H-pyrazol-1-yl]acetyl}-4-fluoropiperidin-4-yl)-N-methyl-N-(1,2,3,4-tetrahydronaphthalen-1-yl)-1,3-thiazole-4-carboxamide (I-6)

The two enantiomers of (±)-2-(1-{[3,5-bis(difluoromethyl)-1H-pyrazol-1-yl]acetyl}-4-fluoropiperidin-4-yl)-N-methyl-N-(1,2,3,4-tetrahydronaphthalen-1-yl)-1,3-thiazole-4-carboxamide (I-4) were isolated by means of chiral preparative HPLC.

EXAMPLES

TABLE 1

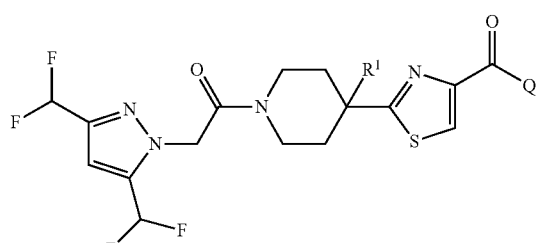

(I-a)

| Example | R$^1$ | Q | logP |
|---|---|---|---|
| I-a-1 | hydrogen | 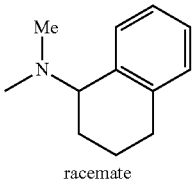 racemate | 3.41 |

TABLE 1-continued (I-a)

[Structure: pyrazole with two CHF2 groups connected via CH2-C(=O)-N to piperidine bearing R¹, connected to thiazole-C(=O)-Q]

| Example | R¹ | Q | logP |
|---|---|---|---|
| I-a-2 | hydrogen | N-methyl-N-(1,2,3,4-tetrahydronaphthalen-1-yl)methylamine, enantiomer 1 | — |
| I-a-3 | hydrogen | N-methyl-N-(1,2,3,4-tetrahydronaphthalen-1-yl)methylamine, enantiomer 2 | — |
| I-a-4 | fluorine | N-methyl-N-(1,2,3,4-tetrahydronaphthalen-1-yl)methylamine, racemate | 3.56 |
| I-a-5 | fluorine | N-methyl-N-(1,2,3,4-tetrahydronaphthalen-1-yl)methylamine, enantiomer 1 | — |
| I-a-6 | fluorine | N-methyl-N-(1,2,3,4-tetrahydronaphthalen-1-yl)methylamine, enantiomer 2 | — |

The log P values were measured according to EEC Directive 79/831 Annex V.A8 by HPLC (high-performance liquid chromatography).

The LC-MS determination within the acidic range is effected at pH 2.7 with 0.1% aqueous formic acid and acetonitrile (contains 0.1% formic acid) as eluents; linear gradient from 10% acetonitrile to 95% acetonitrile.

The calibration is carried out using unbranched alkan-2-ones (having 3 to 16 carbon atoms) with known log P values (determination of the log P values by the retention times using linear interpolation between two successive alkanones). The lambda-maX values were determined in the maxima of the chromatographic signals using the UV spectra from 200 nm to 400 nm.

Specific Rotation

Wavelength: 589 nm; temperature: 20.0° C.; solvent: methanol

| Example | Concentration in MeOH | Specific rotation |
|---|---|---|
| I-a-2 | 95.8 mg/10 ml | −57.2 |
| I-a-3 | 98.3 mg/10 ml | +60.1 |
| I-a-5 | 102.2 mg/10 ml | −54.1 |
| I-a-6 | 107.0 mg/10 ml | +49.8 |

NMR Data

| Example | NMR data |
|---|---|
| I-a-1 | 1.50-2.15 (m, 8H), 2.51-2.88 (m + s, 6H), 3.27-3.40 (m, 2H), 3.89-3.97 (m, 1H), 4.23-4.36 (m, 1H), 5.32-5.38 and 5.80-5.83 (m, 3H), 6.90 (s, 1H), 6.93-7.26 (m, 6H), 8.08 and 8.12 (s, 1H) |
| I-a-4 | 1.50-2.85 (m, 13H), 3.10-3.25 (m, 1H), 3.40-3.55 (m, 1H), 3.80-3.94 (m, 1H), 4.03-4.28 (m, 1H), 5.17-5.53 and 5.77-5.83 (m, 3H), 6.90 (s, 1H), 7.00-7.40 (m, 6H), 8.28 and 8.32 (s, 1H) |

The chemical NMR shifts in ppm were measured at 400 MHz in the solvent DMSO-$d_6$ with tetramethylsilane as internal standard.

Use Examples

Example A

Phytophthora Test (Tomato)/Protective
Solvent: 49 parts by weight of N,N-dimethylformamide
Emulsifier: 1 part by weight of alkylaryl polyglycol ether To produce an appropriate active ingredient formulation, 1 part by weight of active ingredient is mixed with the specified amounts of solvent and emulsifier, and the concentrate is diluted with water to the desired concentration.

To test for protective activity, young tomato plants are sprayed with the formulation of active ingredient at the stated application rate. 1 day after the treatment, the plants are inoculated with a spore suspension of Phytophthora infestans and then remain at 100% relative humidity and 22° C. for 24 h. The plants are then placed in a climatized cabin at about 96% relative atmospheric humidity and a temperature of about 20° C.

Evaluation follows 7 days after the inoculation. 0% means an efficacy which corresponds to that of the control, whereas an efficacy of 100% means that no infection is observed.

In this test, the inventive compounds I-a-1, I-a-2, and I-a-3 exhibit an efficacy of 70% or more at an active ingredient concentration of 100 ppm.

Example B

Plasmopara Test (Grapevine)/Protective
Solvent: 24.5 parts by weight of acetone
24.5 parts by weight of dimethylacetamide
Emulsifier: 1 part by weight of alkylaryl polyglycol ether To produce an appropriate active ingredient formulation, 1 part by weight of active ingredient is mixed with the specified amounts of solvent and emulsifier, and the concentrate is diluted with water to the desired concentration.

To test for protective efficacy, young plants are sprayed with the active ingredient formulation at the stated application rate. After the spray coating has dried on, the plants are inoculated with an aqueous spore suspension of Plasmopara viticola and then remain in an incubation cabin at about 20° C. and 100% relative atmospheric humidity for 1 day. The plants are then placed in a greenhouse at about 21° C. and about 90% atmospheric humidity for 4 days. The plants are then moistened and placed in an incubation cabin for 1 day.

Evaluation follows 6 days after the inoculation. 0% means an efficacy which corresponds to that of the control, whereas an efficacy of 100% means that no infection is observed.

In this test, the inventive compounds I-a-1, I-a-2, and I-a-3 exhibit an efficacy of 70% or more at an active ingredient concentration of 100 ppm.

The invention claimed is:

1. A compound of formula (I)

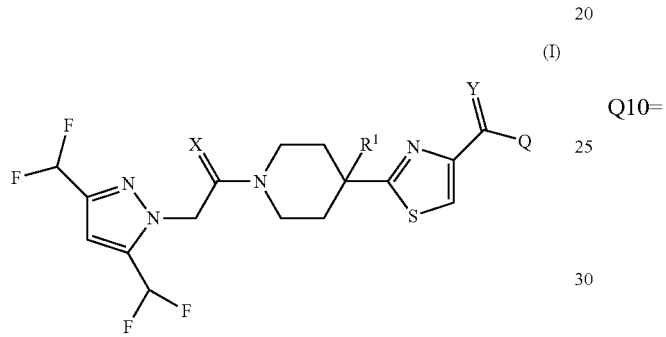

(I)

in which:
X is oxygen or sulphur,
$R^1$ is hydrogen or halogen,
Y is oxygen or sulphur,
Q is —$NR^2R^3$,
$R^2$ is hydrogen, $C_1$-$C_3$-alkyl, $C_2$-$C_3$-alkenyl, $C_2$-$C_3$-alkynyl, $C_4$-$C_{10}$-cycloalkylalkyl, $C_4$-$C_{10}$-alkylcycloalkyl, $C_5$-$C_{10}$-alkylcycloalkylalkyl, $C_1$-$C_3$-haloalkyl, $C_2$-$C_3$-haloalkenyl, cyano, hydroxyl, $C_1$-$C_3$-alkoxy, $C_2$-$C_3$-alkoxyalkyl, $C_1$-$C_3$-hydroxyalkyl, $C_2$-$C_3$-alkylcarbonyl, $C_2$-$C_3$-alkoxycarbonyl, $C_2$-$C_3$-alkylaminocarbonyl or $C_3$-$C_5$-dialkylaminocarbonyl,
$R^3$ is an 8- to 11-membered, unsubstituted or substituted, saturated or partly saturated homo-bicyclic ring system and agrochemically active salts thereof.

2. The compound of formula (I) according to claim 1, in which:
X is oxygen,
$R^1$ is hydrogen or fluorine,
Y is oxygen,
Q is

Q2=

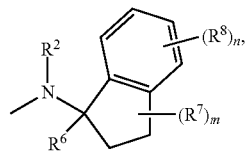

Q5=

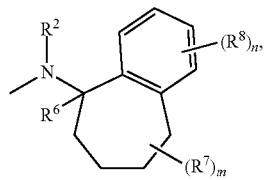

Q8=

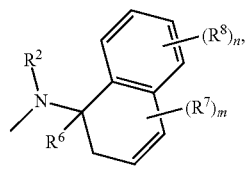

Q10=

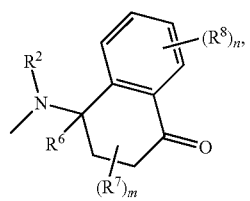

Q11=

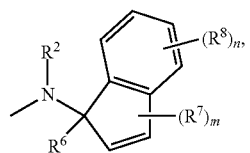

Q13=

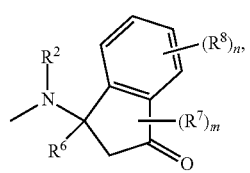

Q14= or Q17=

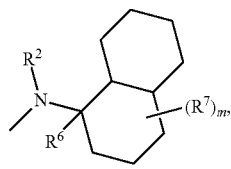

m is 0, 1 or 2,
n is 0, 1 or 2,
$R^2$ is hydrogen or $C_1$-$C_3$-alkyl,
$R^6$ is hydrogen, $C_1$-$C_4$-alkyl, $C_3$-$C_4$-cycloalkyl, $C_2$-$C_4$-alkoxyalkyl, or $C_1$-$C_4$-haloalkyl,
$R^7$ is in each case independently hydrogen, $C_1$-$C_4$-alkyl, halogen, cyano, hydroxyl, amino, nitro, $C_2$-$C_4$-alkenyl, $C_3$-$C_4$-alkynyl, $C_1$-$C_4$-haloalkyl, $C_2$-$C_4$-haloalkenyl, $C_2$-$C_4$-haloalkynyl, $C_3$-$C_6$-cycloalkyl, $C_3$-$C_6$-halocycloalkyl, $C_2$-$C_4$-alkoxyalkyl, $C_1$-$C_4$-alkylamino, $C_2$-$C_6$-dialkylamino, $C_3$-$C_6$-cycloalkylamino, $C_2$-$C_4$-alkylcarbonyl, $C_2$-$C_4$-alkoxycarbonyl, $C_2$-$C_4$-alkylaminocarbonyl, $C_2$-$C_4$-alkylaminocarbonyloxy, $C_3$-$C_6$-dialkylaminocarbonyl, $C_1$-$C_4$-hydroxyalkyl, $C_1$-$C_4$-alkoxy, $C_1$-$C_4$-haloalkoxy, $C_2$-$C_4$-alkylcarbonyloxy, $C_2$-$C_4$-alkylcarbonylthio, $C_1$-$C_4$-alkylthio, $C_1$-$C_4$-haloalkylthio, $C_1$-$C_4$-alkyl sulphinyl, $C_1$-$C_4$-haloalkyl sulphinyl, $C_1$-$C_4$-alkylsulphonyl, $C_1$-$C_4$-haloalkylsulphonyl, or tri($C_1$-$C_2$-alkyl)silyl,
$R^8$ is in each case independently $C_1$-$C_6$-alkyl, halogen, cyano, hydroxyl, amino, nitro, $C_2$-$C_6$-alkenyl, $C_3$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_2$-$C_4$-alkoxyalkyl, $C_1$-$C_4$-alkylamino, $C_2$-$C_8$-dialkylamino, $C_3$-$C_6$-cycloalkylamino, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkyl carbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, or tri($C_1$-$C_2$-alkyl)silyl,
and agrochemically active salts thereof.

3. A method for controlling phytopathogenic harmful fungi comprising applying a least one compound of formula (I) according to claim 1 to the phytopathogenic harmful fungi, their habitat, or a combination thereof.

4. A composition for controlling phytopathogenic harmful fungi at least one compound of formula (I) according to claim 1 an extender, a surfactant, or a combination thereof.

5. A process for producing a composition for controlling phytopathogenic harmful fungi, said process comprising mixing at least one bis(difluoromethyl)pyrazole derivative of formula (I) according to claim 1 with an extender, a surfactant, or a combination thereof.

6. A method for treating a seed comprising applying at least one compound of formula (I) according to claim 1 to the seed in need of such treatment.

7. A method for treating a transgenic plant comprising applying at least one compound of formula (I) according to claim 1 to the transgenic plant in need of such treatment.

8. A method for treating a transgenic seed comprising applying at least one compound of formula (I) according to claim 1 to the transgenic seed in need of such treatment.

9. A method for controlling phytopathogenic harmful fungi, said method comprises applying a least one compound of formula (I) according to claim 2 to the phytopathogenic harmful fungi, their habitat, or a combination thereof.

10. A composition for controlling phytopathogenic harmful fungi comprising at least one compound of formula (I) according to claim 2, an extender, a surfactant, or a combination thereof.

11. A process for producing a composition for controlling phytopathogenic harmful fungi, said process comprises mixing at least one bis(difluoromethyl)pyrazole derivative of formula (I) according to claim 2 with an extender, a surfactant, or a combination thereof.

12. A method for treating a seed comprising applying at least one compound of formula (I) according to claim 2 to the seed in need of such treatment.

13. A method for treating a transgenic plant comprising applying at least one compound of formula (I) according to claim 2 to the transgenic plant in need of such treatment.

* * * * *